US008160351B2

(12) United States Patent
Sandström et al.

(10) Patent No.: US 8,160,351 B2
(45) Date of Patent: Apr. 17, 2012

(54) METHOD AND APPARATUS FOR MURA DETECTION AND METROLOGY

(75) Inventors: Torbjörn Sandström, Pixbo (SE); Lars Stiblert, Göteborg (SE)

(73) Assignee: Micronic Mydata AB, Taby (SE)

( * ) Notice: Subject to any disclaimer, the term of this patent is extended or adjusted under 35 U.S.C. 154(b) by 779 days.

(21) Appl. No.: 12/105,568

(22) Filed: Sep. 8, 2008

(65) Prior Publication Data

US 2009/0028423 A1  Jan. 29, 2009

Related U.S. Application Data

(60) Provisional application No. 60/912,485, filed on Apr. 18, 2007, provisional application No. 60/988,413, filed on Nov. 15, 2007.

(51) Int. Cl.
*G06K 9/00* (2006.01)
(52) U.S. Cl. .................. 382/149; 356/237.4; 356/237.5
(58) Field of Classification Search ............... 356/237.1, 356/239.1–239.3, 239.7, 239.8, 237.2–237.6, 356/600, 601–613, 625, 630–636, 237.4, 356/237.5; 250/559.01, 559.04–559.08, 250/559.11, 559.19, 559.2, 559.24, 559.27, 250/559.28, 559.39–559.45; 382/141, 144, 382/145, 147–149, 152; 348/86, 87, 88, 348/91–93
See application file for complete search history.

(56) References Cited

U.S. PATENT DOCUMENTS 4,958,373 A * 9/1990 Usami et al. .................. 382/149
(Continued)

FOREIGN PATENT DOCUMENTS
JP  10-300447 A  11/1998
(Continued)

OTHER PUBLICATIONS

Kazutaka Tanaguchi et al. *A MURA Detection Method Considering Human Vision Perception*, in Transactions of the Institute of Electrical Engineers of Japan, vol. 126, No. 11, p. 1539-1548, 2006.

(Continued)

*Primary Examiner* — Tarifur Chowdhury
*Assistant Examiner* — Michael P Lapage
(74) *Attorney, Agent, or Firm* — Haynes Beffel & Wolfeld LLP; Ernest J. Beffel, Jr.

(57) ABSTRACT

The invention addresses the lack of comprehensive and quantitative methods for measurements of unwanted visual "mura" effects in displays and image sensors. Mura is generated by errors that are significantly smaller than what is needed for the function of the device, and sometimes smaller than the random variations in the patterns or structures. Capturing essentially all mura defects in a workpiece in a short time requires a daunting combination of sensitivity, statistical data reduction and speed. The invention devices an inspection method, e.g. optical, which maximizes the sensitivity to mura effects and suppresses artifacts from the mura inspection hardware itself and from noise. It does so by scanning the sensor, e.g. a high-resolution camera, creating a region of high internal accuracy across the mura effects. One important example is for mura related to placement errors, where a stage with better than 10 nanometer precision within a 100 mm range is created. A sampling scheme reduces the data volume and separates between instrument errors and real defects based on their different geometrical signatures. The high-resolution camera scans sparse lines at an angle to the dominating directions of expected mura defects, creating extended sensor fields with high internal precision, and quantifying edge placements in small windows in said extended fields. The mura is classified and presented as type, location and severity.

14 Claims, 23 Drawing Sheets

U.S. PATENT DOCUMENTS

| | | | |
|---|---|---|---|
| 5,315,384 A * | 5/1994 | Heffington et al. | 348/93 |
| 5,917,935 A | 6/1999 | Hawthorne et al. | |
| 5,991,038 A | 11/1999 | Yamamoto | |
| 6,154,561 A * | 11/2000 | Pratt et al. | 382/141 |
| 2003/0151008 A1 | 8/2003 | Yamada | |
| 2004/0213449 A1* | 10/2004 | Safaee-Rad et al. | 382/141 |
| 2005/0007364 A1* | 1/2005 | Oyama et al. | 345/428 |
| 2005/0220330 A1 | 10/2005 | Kobayashi et al. | |
| 2005/0271262 A1 | 12/2005 | Yoshida | |
| 2005/0280805 A1 | 12/2005 | Murai | |
| 2006/0158642 A1 | 7/2006 | Tanaka | |
| 2006/0158643 A1 | 7/2006 | Yoshida | |
| 2006/0203246 A1 | 9/2006 | Nakajima et al. | |
| 2008/0199068 A1* | 8/2008 | Duquette et al. | 382/145 |

FOREIGN PATENT DOCUMENTS

| | | |
|---|---|---|
| JP | 2005233869 A2 | 9/2005 |

OTHER PUBLICATIONS

Video Electronics Standards Association (VESA), "Flat Panel Display Measurements Standard (FPDM)", Version 2.0 available online at http://www.vesa.org/public/Fpdm2/FPDMUPDT.pdf. Accessed Nov. 15, 2007.

International Search Report dated Sep. 19, 2008 from corresponding International App. No. PCT/IB2008/001280.

* cited by examiner

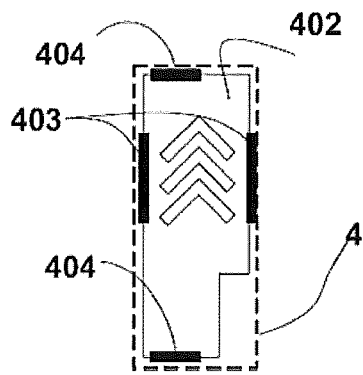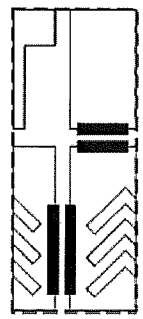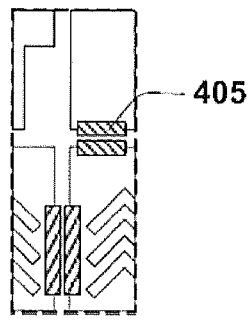
Figure 4a  Figure 4b  Figure 4c
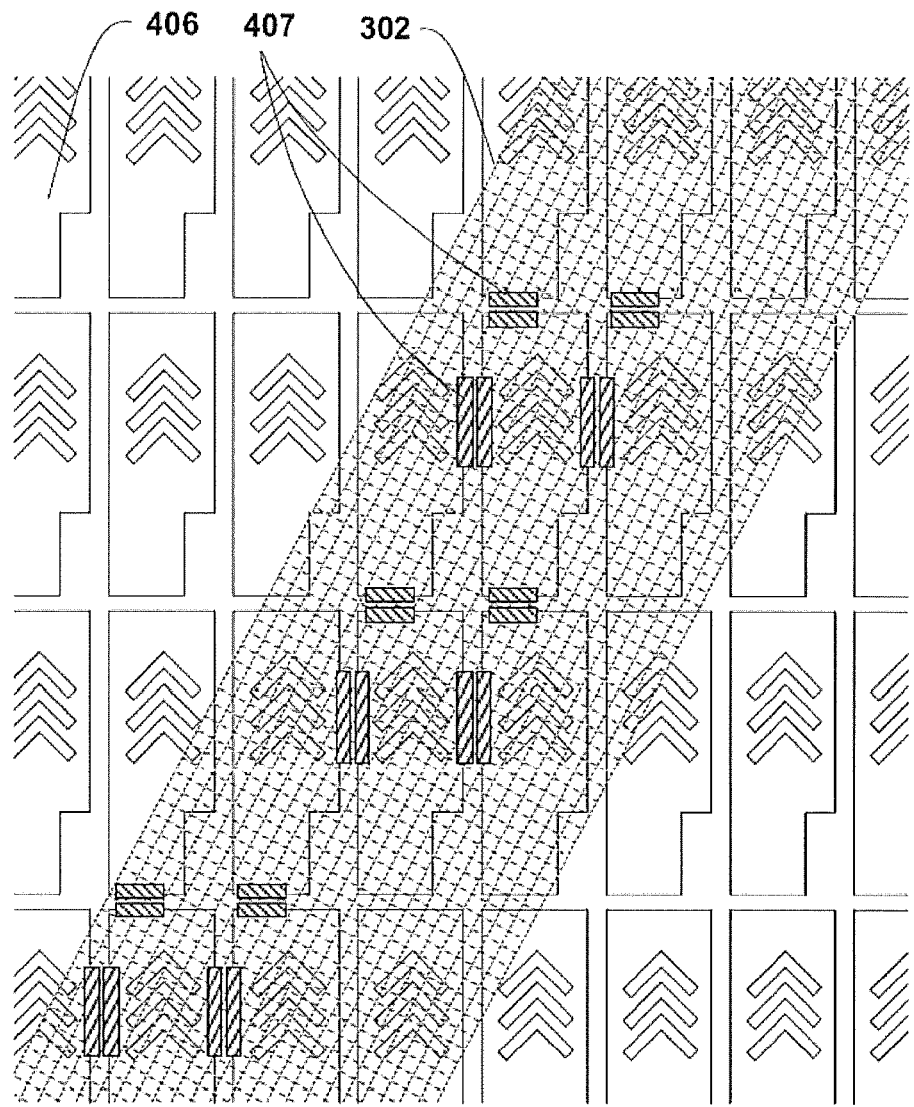
Figure 4d

METHOD AND APPARATUS FOR MURA DETECTION AND METROLOGY

RELATED APPLICATIONS

This application claims priority to two related provisional U.S. Patent Applications: No. 60/912,485 entitled "METHOD AND DEVICE FOR MURA INSPECTION" by inventor s Torbjörn Sandström and Lars Stiblert filed on 18 Apr. 2007; and No. 60/988,413 entitled "METHOD AND APPARATUS FOR MURA DETECTION AND METROLOGY" by inventor Torbjörn Sandström filed on 15 Nov. 2007. The provisional applications are hereby incorporated by reference.

BACKGROUND OF THE INVENTION

This disclosure relates to quality control in the production of extremely accurate patterns, such as those in visual displays (LCD, OLED, SED, FED, PDP, and similar well known display technologies) and image sensors (CCD, CMOS, and other technologies.) The analyzed workpieces may be solid or flexible, and they may be analyzed from the front side or back side. They may be protected by pellicles or other clear sheets at the time of optical analysis. In particular, it provides methods and apparatuses for the detection during production of unwanted visual disturbances potentially occurring in such displays and sensors. The methods and apparatuses may also be used for quality control of memories (SRAM, DRAM, flash, ferroelectric, ferromagnetic, etc.) and for optical grating devices (gratings, DOEs, CGHs, etc.). The methods and apparatuses can be used for testing the finished devices, components used in the finished devices, or for masks and other templates for producing them including templates for imprinting and plates and other master for printing technology.

The disclosed methods and apparatuses are complementary to defect inspection and metrology, two established quality control disciplines in the manufacturing of microelectronic and display devices. Defect inspection can be defined as a complete or sampled search for local defects that will affect the function, typically for defects that will cause catastrophic failure either immediately or later in the life of the product. Defect inspection typically searches for protrusions or mouse bites in pattern edges that are of the order of 25% of the size of the feature. Defect inspection preferably is fast, checking every edge on a workpiece with sometimes billions of features in a few hours.

Metrology, on the other hand, is a very sparsely sampled measurement of the size ("CD"), placement ("registration"), line edge roughness ("LER" and "LWR"), thickness etc. of the features within a pattern. The resolution of line width measurements may in a typical case be 1-2% of the feature width. The measurements are used to validate or adjust the settings of process equipment, e.g., of exposure and deposition systems, plasma etchers, etc. Sampling plans may use eight or fewer measurement sites or as many as a few thousand. Each measured site may take several seconds and a job with several thousand sites takes several hours.

The goal for mura detection and analysis is to find early every occurrence of areas objectionable to the eye. Early means between process steps or after processing but before assembly to modules, so that problems can be found and corrected faster and with less wasted work in progress, and so that material that is useless is removed from the line and not further processed. Mura areas are often areas containing errors that are missed by defect inspection and metrology, errors which have a magnitude far below the detection limit of the defect inspection system, sometimes also below the accuracy of the metrology system, but which affect many features within the area, making that area on average visibly different from the neighborhood. Finding mura preferably relies on a method to accurately measure tens of thousand or hundreds of thousand features within a short time. It requires an extremely low detection limit, often below the stability of the sensor, sometimes even below the noise floor. The noise floor may be due to instrument noise, in which case a more sensitive sensor might be possible, but more often the noise floor is due to randomness in the workpiece. What is random noise and what is mura is then determined by statistics and one aspect of the technology disclosed is to provide methods for sampling mura effect at or below the noise floor and to discriminate them from the noise.

FIG. 1b shows in an approximate way the relation between defect inspection, CD and registration (placement) metrology and mura detection. The figure shows the needed sensitivity/accuracy, the lateral range over which the precision/accuracy needs to be maintained and the portion of the area of the workpiece that needs to be sampled in a quality-control situation.

Visual devices, both displays and sensors, are much more sensitive to certain small errors than e.g. microprocessors or electronic interconnects. Visual displays have an analog character. The eye is sensitive to intensity variation down to a fraction of a percent, while electronic circuits typically have tolerances of the order of 10%. Furthermore, electronic malfunctions are usually due to isolated errors, e.g. line width errors, while in visual displays the errors are averaged over some area by the visual system. An exception from the relative insensitivity of electronic devices is memories where a memory cell can be designed with more speed and smaller size if the tolerances from cell to cell and from line to line can be made smaller. Visual defects are often called "mura" after a Japanese word meaning defect, deficiency, or lack of quality.

Visible errors or variations in a display may occur under different conditions: at perpendicular or oblique illumination; at perpendicular or oblique viewing; in reflection or transmission; in light, dark, or gray areas; as shifts in intensity or color, etc. Finished modules may be tested automatically for lines, spots and blemishes, as described in U.S. Pat. No. 5,917,935 assigned to Photon Dynamics. Typically, a high-quality color camera takes an image of the finished module and visual defects are identified and classified based on image processing of the luminance image. In the Flat Panel Display Measurements Standard (FPDM) published by the Video Electronics Standards Association (VESA), unwanted luminance structure or variation in a finished module is classified into 23 classes using a classification by applying 15 rules. Version 2.0 available online at http://www.vesa.org/public/Fpdm2/FPD-MUPDT.pdf, accessed 15 Nov. 2007. Software and hardware for mura detection in display modules are sold by the companies Orbotech, Israel, and Photon Dynamics, USA. The classes are of the type "thin horizontal line", "wide horizontal line", and "bright region", and the classification relates to typical electric malfunction or variability exemplified by "row line" and "panel driver block" in a technical note from Photon Dynamics.

In the paper *A MURA Detection Method Considering Human Vision Perception* by Kazutaka Tanaguchi et al. in *IEEJ Trans IA*, Vol. 126, No. 11, 2006 a mura detection system based on luminance analysis of the transmission through a shadow mask is described.

One potentially large source of mura is the photomask. Current quality control of masks is mainly manual and visual. The pattern, e.g. a mask pattern, is inspected in reflected, transmitted, and scattered light with monochromatic or white light illumination. The person inspecting the pattern is moving the mask and the illumination in many combinations, and if none of them shows unwanted visible effects the mask is deemed to be OK. This is not an ideal test method. It is non-quantitative, forcing the inspection person to be very conservative in their judgment. There is no clear coupling between what is seen and how it affects the performance of the finished device. The method is very sensitive for certain types of errors and not for other types. In particular, it is more sensitive to line width and edge effects than to displacement errors. Inter-layer errors go largely untested and undetected.

Prior art in instruments for pattern-related mura detection in masks can be represented by JP25233869A2, which describes a computerized light table forming and capturing a monochromatic image in diffracted light. This is essentially a mechanized version of the manual procedure. The image is captured perpendicular to the workpiece which is dark-field illuminated from an angle theoretically determined to give high sensitivity to line width variations. A camera records an image through a lens stepped down so that single pixel cells in the mask are not resolved. The result is a uniform gray image. If there is an area where the average line width is larger the gray tone of that area is darker or brighter. The method is extremely sensitive, down to a nanometer line width variation or below, but the sensitivity needs to be calibrated for the particular pattern that is inspected. After calibration, it is quantitative. Moreover, while it is sensitive to line width and edge quality, it is only sensitive to sharp steps in the placement of features, thereby largely missing interlayer effects.

Other prior art is described in U.S. Pat. No. 5,991,038 (priority from JP-A-10-300447.) A camera looks at the workpiece at low magnification and captures light scattered into a non-specular direction. A TDI (time delay and integrate) sensor is used to create a sharp and undistorted image, despite the oblique angle of observation and the use of a non-telecentric lens. Publications US2005/0220330, US2006/0158642, US2005/0280805, and US2005/0271262 describe various improvements over the method in U.S. Pat. No. 5,991,038: using a parallel illumination beam, inspecting from the back side of the substrate, calibrating the scattered light measurement by a physical reference, and classifying the detected errors by comparison to a physical reference.

Furthermore, U.S. Pat. No. 5,991,038 describes a tandem system with both oblique angled observation at low magnification and unresolved pattern and a perpendicularly arranged high-resolution camera for looking at the shape of features. US publication 2006/0158643A1 also has an overview camera and a microscope which shoots the image of the inspected area and extracts information, e.g. shape and pitch, and displays it on a display device.

BRIEF DESCRIPTION OF THE DRAWINGS

FIG. 2d shows a system where the machine axes of movement are neither parallel nor perpendicular to the 0, 90 and 45 degree directions on the workpiece. FIG. 2e shows an example embodiment with two cameras moving on two beams. FIG. 2f depicts details of an example embodiment of a beam system with high precision over a long distance.

In FIG. 3b the measurements along three stripes are shown. FIG. 3c shows how the mura line indicated in FIG. 3a can be found and identified by filtering the data for errors that occur at the same x coordinate.

FIG. 4a shows a typical LCD pixel cell and how edges suitable for measurement can be defined. FIG. 4b shows an alternative definition of the repeating cell and how the edges may be defined. FIG. 4c shows how the corresponding measurement windows can be defined. In FIG. 4d, an extended camera field forms an oblique stripe and only the pixels inside the measurement windows defined in the sampling plan need to be captured.

FIG. 9f shows more specifically how 2D areas of high internal precision are formed.

DETAILED DESCRIPTION

Figure 1A:
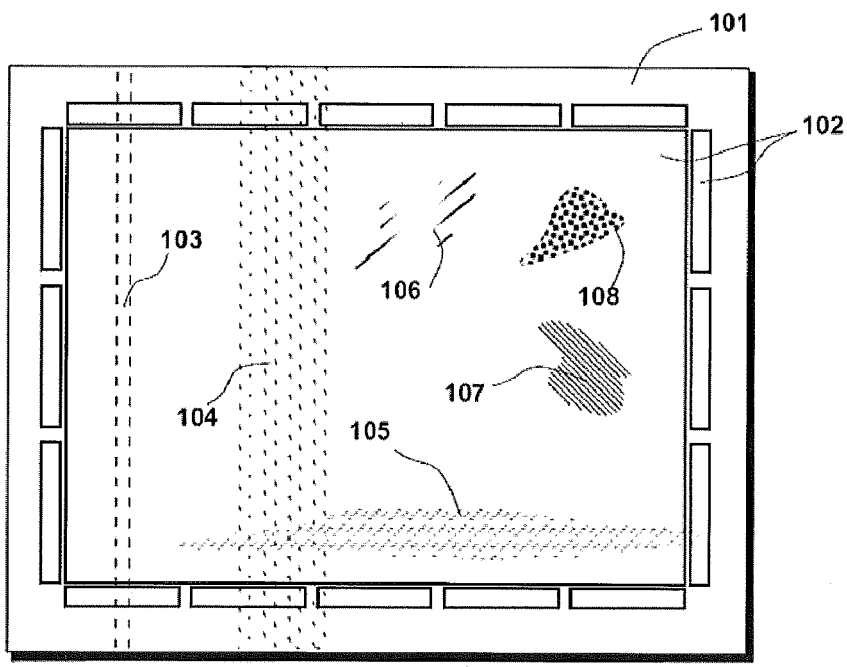
FIG. 1a shows a workpiece with an LCD pattern on it and a number of often occurring mura effects.

The following detailed description is made with reference to the figures. Preferred embodiments are described to illustrate the present invention, not to limit its scope, which is defined by the claims. Those of ordinary skill in the art will recognize a variety of equivalent variations on the description that follows.

The underlying errors causing the mura may be of many kinds, only some of which have been recognized or understood in the art. One cause is a variation in the open or light sensitive areas, e.g. a variation in the width of the black matrix masking the transistor and the boundary between pixels in an LCD display. Every pixel in an active display has at least one transistor with a gate which is much smaller than the size of the LCD pixel, thereby being much more sensitive to line width variations. The edge profile of the different layers may also vary and give rise to mura. Line width, shape and edge variations are intra-layer effects, i.e. they can be detected in a single layer, e.g. in a photomask. A second source of mura defects is inter-layer effects: relative displacements between two layers affecting the electronic function of the pixel cells or the capacitances in the cells. These are typically displacements of features in the patterns. A driving voltage range of 20 V will cause a transmission difference of more than 1:1000 in an LCD screen. A simple model where the transmission is proportional to $\cos^2(c*V)$, where V is the applied cell voltage and c is a constant fitted to give zero transmission at 20 V, shows that a 20 mV or 0.1% voltage difference gives a 1% change in transmission at 10% gray. This is consistent with the fact that high-quality displays use 10, 12, or even 14 bits internal bitmap processing in their internal electronics and that new image formats are being introduced (e.g., HD Photo by Microsoft, USA) with more than 8-bit color depth. A back-of-envelope calculation shows that LCD screens are not only analog in character, but do actually amplify errors. Other errors arise from variations in film thicknesses, sheet resistance, surface energy, mechanical strain and similar non-pattern or non-geometrical effects.

A brute force approach to quantifying mura effects is often intractable, especially those effects related to line width and placement. The needed sensitivity for CD and placement errors in an LCD mask or panel may be below 10 nm. Measuring the placement of all edges in a photomask or panel with this precision would need high-resolution optics with a small field and scanning the entire surface would take too long time. It would also require a 2D metrology stage with a coordinate system stable to 10 nm or better. The workpieces are roughly 1×1.5 m (masks) and 2.5×3 m (mother glasses for panel production) and the needed stability is difficult and expensive to achieve, if at all possible.

It would be useful to make predictions of mura which will occur in the finished modules before the modules are assembled based on an optical or physical analysis of the glass panels or of the masks or templates. It also would be useful to analyze the films and patterns on the glass to find the root causes of problems that have been unveiled in module inspection. What is said about display modules also applies to image sensors and masks for memories.

The methods and apparatuses described create local areas of high internal precision in order to measure variations in the pattern with extreme precision in these areas. The movement system that creates the local areas of high internal precision is designed to give different signatures for typical errors from those of mura effects of the workpiece. Mura effects are computed from measured data within the areas of high internal precision. The workpiece is sampled sparsely by a sampling plan designed to capture typical mura effects. For embodiments targeting placement errors, a semi-locally accurate coordinate system is created and a sampling plan which can find all commonly occurring types of mura with a reasonable number of measurements. Furthermore, the sampling described below reduces the amount of data that needs to be analyzed per sampling site by two orders of magnitude. The combination produces a several-orders-of-magnitude reduction of the problem, a reduction which makes the use of high-resolution imaging affordable. The method is flexible and can be modified by the operator to trade between the sensitivity and comprehensiveness on one side and the time to analyze a work-piece on the other.

The method disclosed samples the workpiece, e.g., a glass panel or a photomask, by a movement of the sensor within a region of high internal precision. An example embodiment has a small xy-stage with high precision movements, e.g., better than 10 nm precision, and the pattern in a small area, e.g., less than 100×100 mm, is sampled. The axes of the xy-stage may be non-parallel to dominating directions of mura and the mura properties of the workpiece may be calculated using a priori knowledge of the dominant directions of the mura. The stage is moved sequentially to different sites on the workpiece, so that several areas are measured. Sampling of areas on a workpiece is illustrated in FIG. 1c. The workpiece 101 is analyzed by the sensor 109, which can be positioned in the positioning coordinate system 111 by a movement system 110. The positioning system may not have enough stability or precision to support the measurement of mura effects in the workpiece 101. After the camera has been roughly positioned, a high-precision system depicted as a small stage 113 with a high-precision coordinate system 112 scans an area and establishes an area of high internal precision 114 in which the mura is measured. The small stage is moved to other areas 115 of the workpiece so that the area is sampled by high-precision measurement densely enough to capture all or nearly all of the mura 103-108 in FIG. 1a. Since the typical mura errors have a finite geometrical size, the scanned area will be smaller than the total area of the workpiece and methods to sample the area efficiently will be discussed below.

In another example embodiment, the sampling is done in lines, e.g., sparse lines, by a scanning stage. Depending on the sensor, these lines can be narrow true 1D lines or be stripes with a finite width. At least some of the lines are piece-wise non-perpendicular and non-parallel to at least some dominating directions of mura in the workpiece. For an embodiment where lateral positioning the sensor is not critical, e.g., a scatterometer sampling an area several square millimeters wide, the lines can be curved, e.g., circular, sinusoidal, or irregularly curved. For measurement of placement, the preferred movement is linear. The relative movement of the sensor versus the workpiece may be created by moving the sensor, the workpiece, or both.

The a priori knowledge of dominating directions of mura can be gained from the design of the process equipment, e.g., the hardware of the exposure tools, from past experience with similar processes and workpieces, or from 2D spectral analysis of a workpiece. Using a spectral analysis to establish the dominating directions of variations may be time-consuming, but once the dominating directions are established a sparse sampling plan can be set up and the scanning and analysis may be fast. The most severe mura effects are horizontal or vertical lines or bands. Scanning through such a line or band at an oblique angle will give a profile along the scan line. The sensor will within a short time span sample the workpiece on one side of the mura-affected band, inside the band, and on the other side of the band. Because of the short distance and time required, there will be little instrument drift while scanning the three areas. The background variation due to process variations over the surface will be small. A second line is scanned parallel to the first one some distance away. It will, if the mura is a band extending from side to side of the workpiece, measure the same behavior in both lines, and conclusions can be drawn about the existence and shape of the mura band, even if in a single measurement it is hidden in measurement noise. More parallel lines gives more noise suppression following the laws of statistics.

For placement errors, the method disclosed uses edge-by-edge image processing in a high-resolution camera image to quantify the line width and placement, and, optionally, edge quality of pattern features. It does so with unprecedented speed, efficiency and accuracy. The data is mapped and analyzed for the spatial signature of the expected mura effects. The method is designed so that typical artifacts of the metrology system have other signatures and can be removed from the data. Aspects of the method can also be used for non-optical, non-geometrical, or non-pattern-related measurements of potentially mura-generating properties using other sensors than a high-resolution camera, e.g., an interferometer, a scatterometer, a reflectometer, a polarimeter, a calorimeter, a spectrometer, a thickness monitor, an electric, mechanical, hydraulic, pneumatic, chemical, or acoustic sensor, a surface or composition analysis sensor, an atomic force or other near-field probe, etc. Application of these sensors will be described below.

A high-resolution camera has a small field. Its field is extended by a mechanical movement of the measuring camera relative to the workpiece. This may be a simple mechanical movement with high precision along one degree of freedom. One possible movement would be the rotation of the camera around a fluid bearing, creating an arc with high precision. Another movement would be the sliding of the camera unit along a beam, creating a straight line with high precision both along and across the direction of movement. In both cases an extended camera field results.

Often mura effects are one-dimensional lines or stripes along the Cartesian axes of the workpiece due to the scanning motions in the mask writer and the exposure tool, to the axes of the interferometer, to the movement of the guides in the stages, to typical patterns with both edges and repetitions along the Cartesian axes, etc. The rubbing used to orient the liquid crystal molecules, the polarizers, the illuminator, and moiré effects may give mura with a dominating 45 degree direction. Ideally the extended camera field (or extended sensor or probe field) crosses all these dominating directions of mura at an angle, so that stripes or lines along the dominating directions give a measured profile along the extended field. With a linear motion extending the camera field to an image stripe, the stripe is along a direction which is not parallel to the Cartesian axes 0 and 90 degrees of the stage, maskwriter, pattern, etc. It may also be chosen to be non-parallel to 45 degrees and any other direction where mura bands are expected to occur.

The errors are sampled according to a sampling plan which depends on the movement. A list of edges (or other areas, see below) to be measured inside the extended field is generated and a data window is defined around each of them. The pixels in the extended field may be thrown away, except for the pixels that are inside the data windows. The edge position is determined in each window. This can be done using known techniques of data cleaning, noise reduction, model fitting, and subpixel interpolation. This processing can be done rapidly, since, after an initial alignment procedure when the coordinate system in the computer is adjusted to the placement of the workpiece on the stage, the position of an edge relative to the camera is known to be better than one camera pixel. The measured data may be analyzed in real time and the alignment of the coordinate system may be updated dynamically on the basis of the measurements. When the sensor or camera passes over areas without pattern or if it misses a measurement, the path is predicted based on extrapolation of the previous path and on known distortions in the system and workpiece. As soon as pattern becomes available, the system can synchronize to the pattern and adjust its internal coordinate system without stopping. This is done at scanning speed and constitutes a an on-the-fly "in-cell" alignment system which may be used independently from mura detection, e.g. in exposure systems based on masks or digital patterning description, e.g., mask writers, direct-writers for wafers, panels, MCMs, PCBs, etc. It may also be used for registration metrology, in particular for fast registration metrology, e.g., in-line metrology of the registration of panels used in displays.

The method and apparatus disclosed allow a system to be built which quantifies a wide variety mura effects in a mask or a production panel or wafer. For mura effects caused by placement errors, it may have a sensitivity below 10 nm and the time to find essentially every significant occurrence of mura may be below one hour per square meter. Furthermore, the mechanics and data processing are significantly simpler and less costly than some other approaches with the same sensitivity. Finding mura early saves money and increases the yield in production of masks, displays and semiconductor devices, giving better production economy and easier tuning of production equipment. In the end this leads to higher-quality devices and lower prices for the consumer.

Figure 1B:
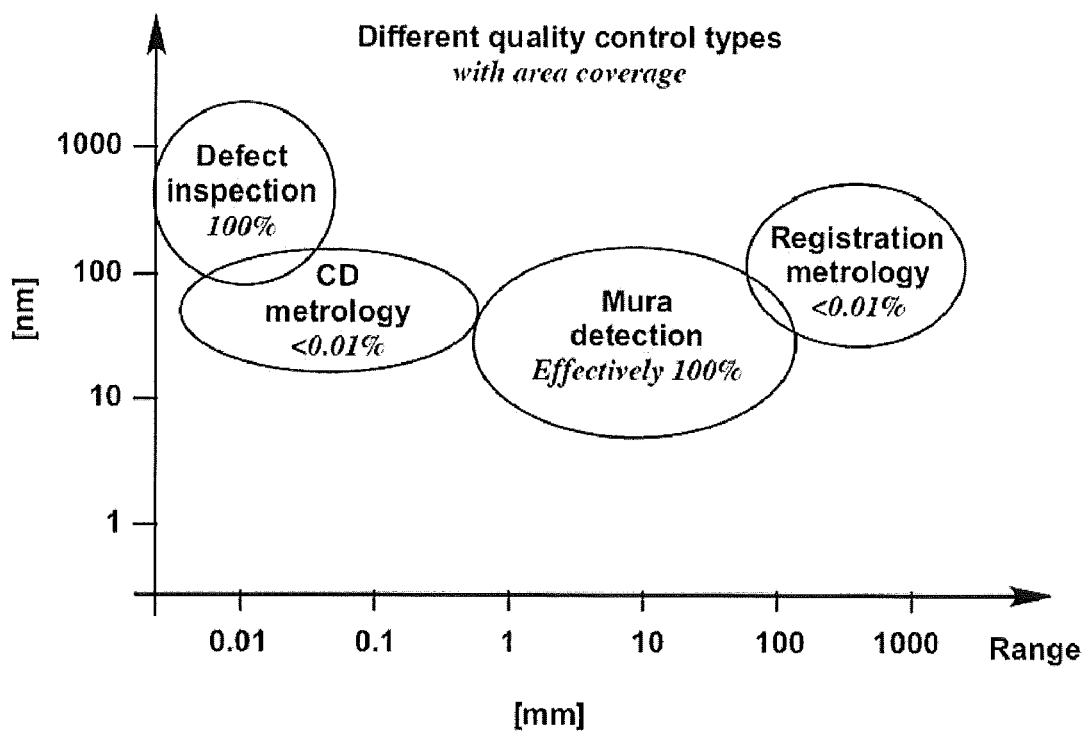
In FIG. 1b, typical operating requirements for different types of quality control systems are shown.
Figure 1C:
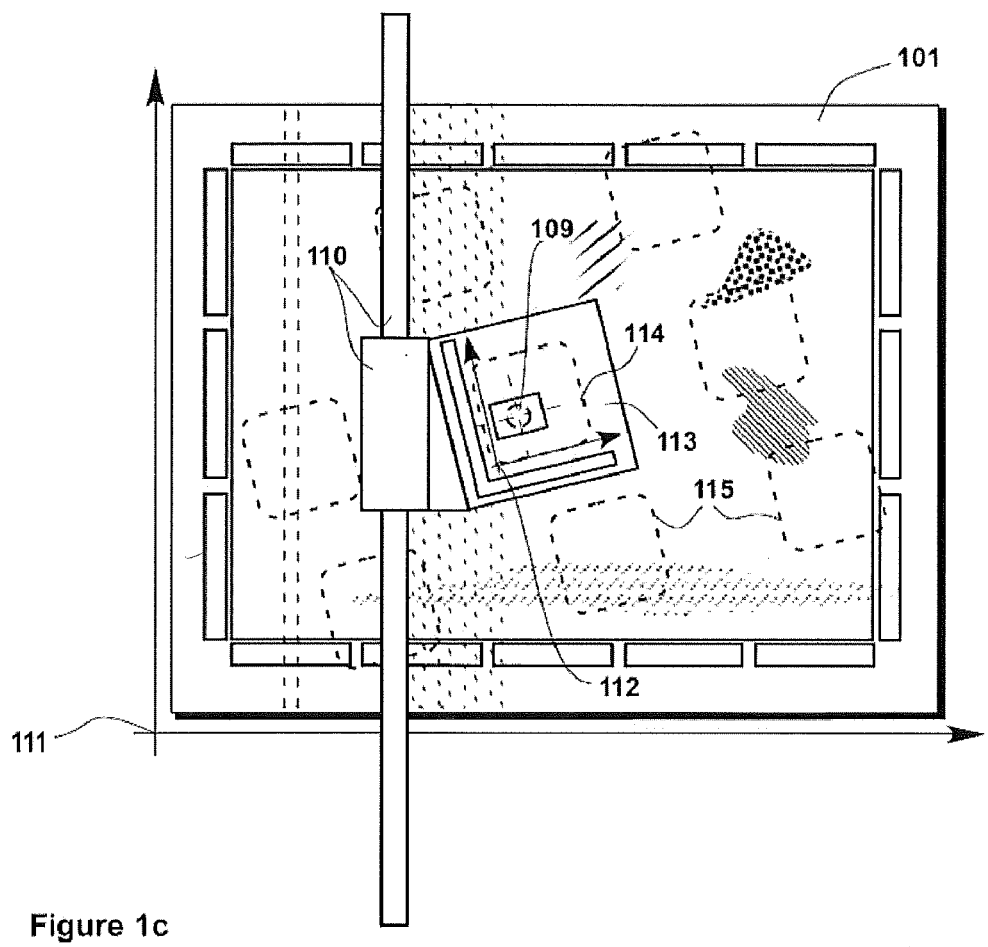
FIG. 1c is a conceptual view of how mura is found efficiently by scanning sample areas with high internal precision at various locations across the surface of the workpiece.

FIG. 1 shows in conceptual form a substrate 101 with a pattern 102 and a number of mura effects 103-108. One type of mura is a single line 103 along one Cartesian axis e.g. due to a maskwriter malfunction or a stitching error in the exposure tool. Repeated lines parallel to a Cartesian axis 104 may be due to moiré between the pattern and the design grid, interferometer non-linearity, etc. Vibrations during mask-writing or exposure may give periodic wave-like effects 105 along one Cartesian axis. Defects in the polarizer or inadequate rubbing may give 45 degree artifacts 106. Finally, it is possible to have large or small patches with different properties 107 or inhomogeneity 108 as a result of material or process equipment problems.

Variations that lead to visible mura may have spatial frequencies between 2 per millimeter and 1 per 100 mm, depending on the application of the display and the distance from the eye. Lower frequencies are generally less well visible and higher frequencies are not resolved by the eye. In order to measure placement errors, leading to inter-layer mura, with a frequency down to 1 per 100 mm a stable mechanical stage is needed. FIGS. 2a, 2b, 2c, 2d, 2e and 2f show a simple stage which has high precision, but moves in one direction only. A camera 201 (or generally any sensor) slides along a straight beam 202. The beam, which may be made from a ceramic material with high specific stiffness and low thermal expansion, is ground and polished straight and the camera slides on air bearings. If the air bearing pads, e.g. porous pads available from several companies such as Nelson Air, USA, are 100 mm or longer they integrate the remaining high-frequency shape errors of the beam. The result is a not necessarily straight but extremely smooth movement of the camera. Along the beam the movement is controlled by a length encoder, shown here as an interferometer 204 measuring the distance 203 to the lens. Other encoders that have nanometric resolution and short range precision such as some glass scales may be used. The workpiece is positioned under the camera and suitable clamping and climate control are provided. Example embodiments where the camera is fixed and the stage does the scanning or the scanning is the result of a combined movement of stage and sensor are possible.

It may be impossible to build the system with perfectly straight and even travel even over short distances. However, a calibration of the movement can be obtained and maintained by integration of all measurements. As will be discussed below the signature of errors in the movement system are different from errors typically occurring in the workpieces to be analyzed. During the measurement of a single workpiece significant calibration information may be gathered and a refined calibration may be accumulated during subsequent jobs.

Figure 2F:
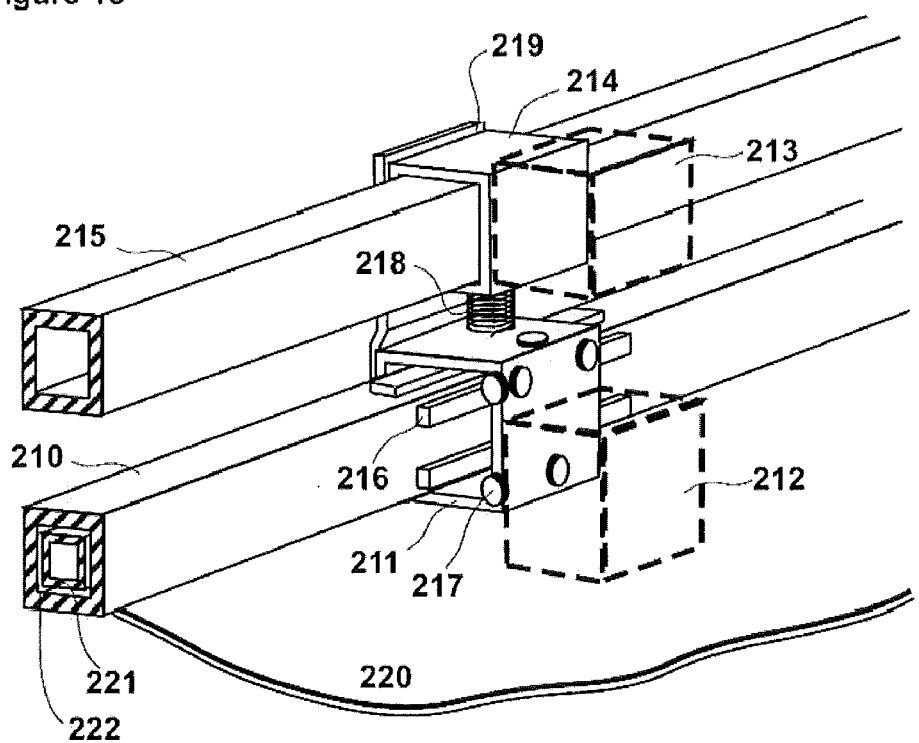
FIGS. 2a, 2b, 2c, 2d, 2e and 2f show mechanical systems for linear high-precision movement of a camera over a workpiece in different directions: parallel to the short side (2a), parallel to the long side (2b) and at a direction that is non-parallel to both edges and to the 45 degree diagonal (2c).
Figure 2A:
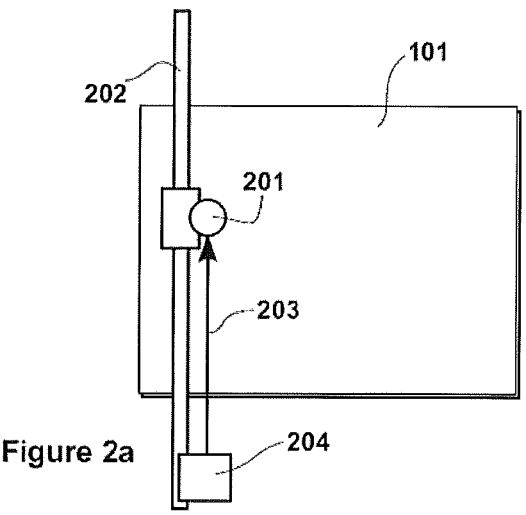
Figure 2B:
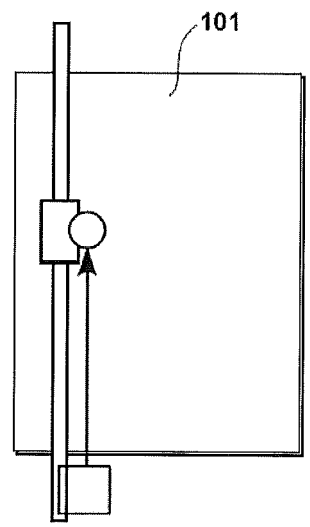

In FIG. 2a the camera scans parallel to the short side of the workpiece 101. The camera may now find the mura lines in FIG. 1a that it crosses 105, but it may miss 103. Even if it scans the entire glass surface the sensitivity to 103 will be reduced by the fact that it does not scan across the mura line 103 and a relevant background close in time and repositioning errors and mechanical drift create too much uncertainty. Turning the workpiece by 90 degrees will reveal 103 and 104, but may now miss 105. The defect areas 107 and 108 may be found in both 2a and 2b, if the sampling of the pattern is dense enough.

Figure 2C:
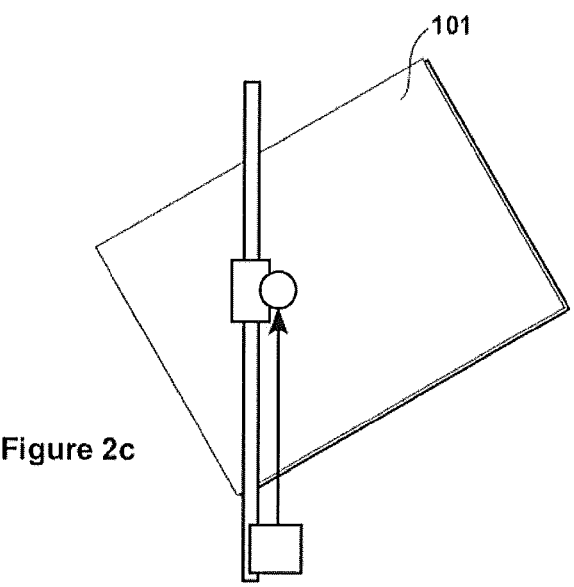
Figure 2D:
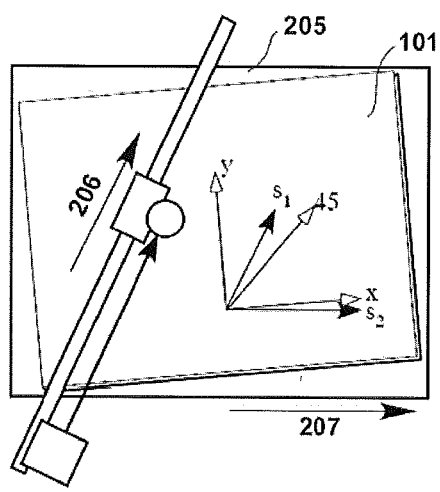

Running the camera at an oblique angle as in FIG. 2c will find all mura errors in FIG. 1a. The line 103 is measured and a relevant background is measured a few milliseconds before and after it. The same is true for 105. The scanning system is built to maintain nanometer stability over 100 millimeters along the beam and in 100 millimeters it will cross through faulty areas and reference areas. Areas that do not vary over 100 mm are less critical to the eye and the reduced accuracy over longer distances may capture the larger magnitudes that will cause visible effects. Typical errors generated by the movement system itself will be along and across the beam and with different spectra. They can at least partly be removed since they have a different signature, which is typical of them alone. FIG. 2d shows how the movement between the scan lines is not parallel to the x axis of the plate in order to better separate movement errors and workpiece errors.

Figure 2E:
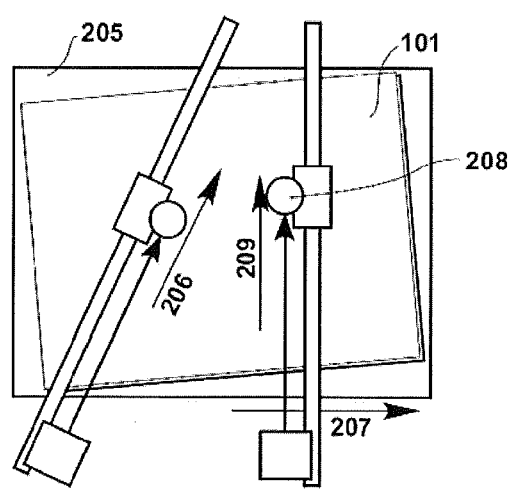

In some applications there is a need for a larger area of high internal precision that is more than one stripe wide. FIG. 2e shows an example embodiment with two sensors on two beams, and one sensor may conceptually be though of as an auxiliary measurement which determines the position of the stripes scanned by the first camera, thereby extending the area of high internal precision in the direction perpendicular to the stripes from the first camera.

Figure 3A:
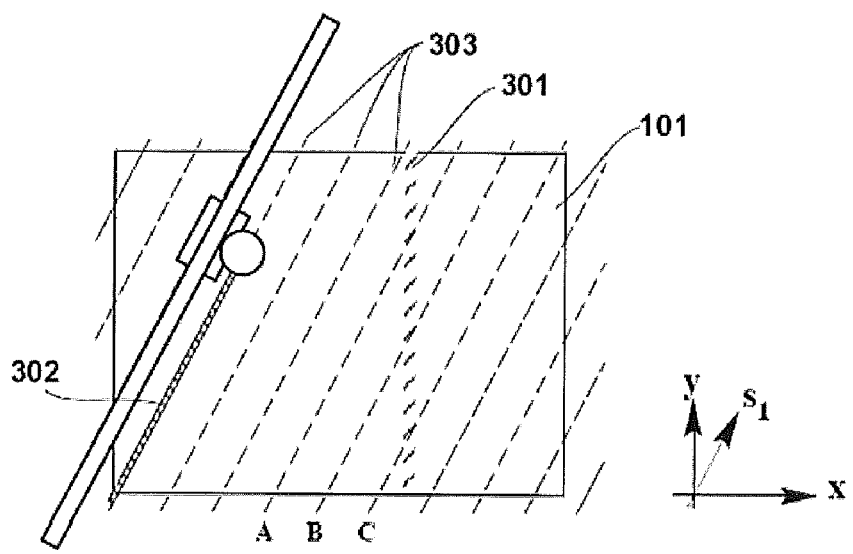
FIGS. 3a, 3b, and 3c show how the camera field (or more generally the measurement field of any sensor) is extended to a stripe and how a number of these stripes sample the area.

FIG. 3a shows how the camera field is extended into a stripe 302 by the movement 302. The area of the workpiece 101 is sampled by multiple stripes 303. The sampling plan set up when the job is planned defines how dense these stripes will be and how many edges in each will be analyzed.

Figure 3B:
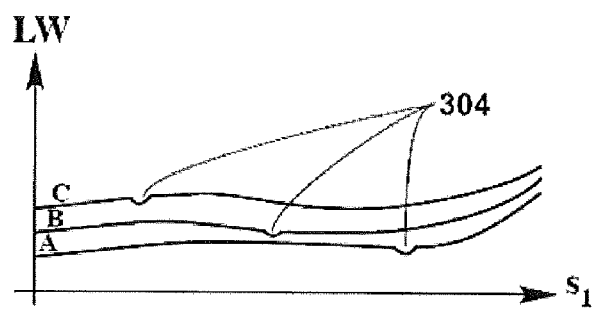

As an example of the function assume that the workpiece 101 has a line defect 301 which is crossed by three stripes A, B, and C in the sampling plan shown in FIG. 3a. FIG. 3b shows how the measured line width LW varies along the stripes A, B, and C. Some of this variation is real, but may not be important due to the low frequency, and some of it may be generated by the measurement system. It is shown in FIG. 3b that there are 3 dents 304 in the curves. If they are seen in each individual curve they might be attributed to noise, but replotted in FIG. 3c with the x coordinate on the horizontal axis they line up and can be identified as the line defect 301 in position 305.

Figure 3C:
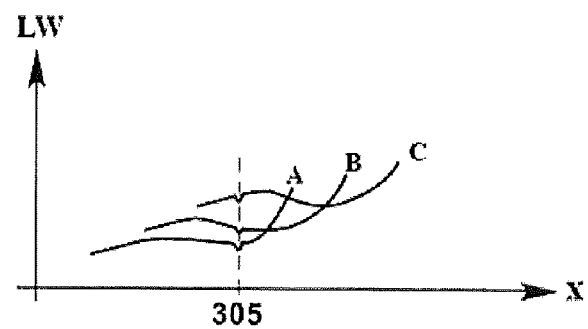

FIGS. 3a, 3b, and 3c show a procedure that is illustrative. Some embodiments may be more abstract and algorithmic and less based on graphics than others. One approach is to map the measured parameter, here line width, on an xy plane and remove the background with a high-pass spatial filter such as a Fourier filter, then search for mura-like features in the remaining image. Another preferred and more general approach is to record every measurement with its x and y coordinates, its distance along the beam, the position in the camera field, the time-stamp when it is measured, the air pressure, and so on. If the mask writing parameters are known the position in the mask writer field may be tabulated as well. This table is analyzed by multivariate analysis, singular value decomposition or other statistical methods to find how the measured parameter depends on the different parameters. One of the outputs is mura as stripes or areas in the xy plane, other outputs is linearity of the camera and maskwriter fields.

Once the mura areas are identified they may be categorized by the type of mura and its severity. This becomes the output of the measurement to the operator: detected mura instances with type, location and severity. Additional information may be produced: line width average and variation, placement jitter, etc.

FIG. 4 shows some details about the sampling plan. FIG. 4a shows a unit cell 401 in an LCD screen, an LCD pixel. Not all edges of the pattern feature 402 may be suitable for analysis. The required sensitivity is very high and selecting good and stable edges in balanced pairs 403, 404 in the unit cell is one way of reducing spurious variance. FIG. 4a shows a cell with chevrons which are not measured. In a different measurement job the chevrons could be included or measured exclusively. The edge measurement to be described below can measure edges in any angle.

In a repeating pattern the repeating unit can be chosen in many ways. FIG. 4b shows a differently defined unit cell of the pattern as in FIG. 4a where the two parallel and balancing pairs have the balancing edges close together. This may make the spurious errors form process variations smaller. In FIG. 4c the edges to be measured are assigned windows which will act as data windows in the bitmap. Only those pixels with center points inside the windows are retained and used for the analysis. Finally in FIG. 4d the bitmap from the extended camera field 302 is shown. A number of the unit cells within the extended camera window are selected for measurement and data windows 407 are assigned bitmap areas in those cells. The simplification of the task is shown by the area of the extended camera window compared to the entire workpiece and by the area of the measurement windows compared to the entire camera field. Furthermore, the system knows beforehand the placement of every edge within one camera pixel and the edges hardly change from one LCD pixel to the next LCD pixel, so the determination of the edge location in each data window consists of a small adjustment to an already very good starting guess.

Most machine vision systems have the pixel grid of the camera parallel to the axes of the workpiece. In many cases it is a natural choice to have it parallel to the mechanical scanning motion. It should be suitable to make the camera coordinate system in an embodiment non-parallel to the Cartesian axes of the workpiece. Oblique stripes scanned by a TDI camera produce a bitmap which is oblique to Manhattan-oriented edges in the pattern on the workpiece. The features will lock rotated by the stripe angle in the bit-map as shown in FIGS. 5a-5g. This is mostly advantageous, since along the edge there is a systematic cancellation of grid effects allowing the grid to sample the edge with coarser pixels that an a bit-map aligned to the edges would allow. The angled measurement has the additional benefit that an algorithm which works for an unspecified angle works for other angles as well, e.g. it can measure both the outer edges 403, 404 and the chevrons in FIG. 4. FIGS. 5a-5g show some details of a preferred embodiment of the edge location determination.

The camera has a pixel grid 501 that may be extended across the entire extended camera field, i.e. typically from side to side of the workpiece. A feature 502 has one edge which is designated to be measured. The sampling plan defines the data window 503 and the expected edge position 504. The camera pixels with centers inside the window are captured into memory. The analysis of the edge location can be done with commercial or open-source software, e.g. Sapera from Dalsa or NI Vision from National Instruments, both from USA, or with the method described below.

In a preferred embodiment the following analysis is performed to find the location of an edge: For each pixel $p_i$ in the window the pair $(I_i, a_i)$ is formed where I is the camera intensity and a is the placement orthogonal to the expected or nominal edge position 504. A model edge may be fitted to the collection of pairs with a weight function with is high near the expected line and has zero weight at the edge of the window, e.g. a Gaussian function centered around the line 504. Alternatively the derivative dI/da (dashed line in FIG. 5$b$), may be used as a weight function. The model edge, the solid line in FIG. 5$b$, is combined with an pre-defined threshold value 505 and gives the edge location 506. If the edge so determined is within a predetermined distance from the nominal position the value is accepted, otherwise the procedure is repeated with the nominal edge position 504 moved to 506. The correction of the nominal position centers the weight function on the actual edge, making sure that the measurement data used is the most relevant one.

The image of edges look differently depending on the character of the abutting areas and the shape of the edge, from the drawn dark-to-bright transition over low-contrast non-monotonic edges between two materials to the thin dark line of a pure phase step. It is the function of the edge model to adapt the measurement to the actual edge. If the edge is monotonic like in FIG. 5$b$ the model corrects for the dark and bright levels and sets a threshold 505 between them. For a dark line it is more appropriate to set the dark level on a dark reference area somewhere else in the image and to find the location as the symmetry point between two locations where the intensity crosses the threshold. Most edges will fall in these categories or a combination of them. An optional aspect of the technology disclosed is to provide an edge model that handles these and more complex edges in a unified way. FIG. 5$e$ shows conceptually a trace across a more complex edge 520. FIG. 5$f$ shows three different edges, a simple transition 521 (solid), a bright line 522 (dashed), and an edge with a third order behavior 523 (dot-dashed) which can be view as mathematical components in the actual edge 520, i.e. the edge is the sum of the three components with coefficients and displacements added. If the component edges 521, 522, and 523 are integrated across the edge the turn into the functions 524, 525, and 526, as shown in FIG. 5$g$. We see that the bright line 522 has integrated to something that looks like the simple transition 521. Integrating once more, FIG. 5$h$, gives 527, 528, and 529 where 529 looks like the transition 521. If the measured edge is decomposed mathematically into the different-order edge types, and each of them are processed numerically, e.g. by integration one or more times, to yield a transition-like curve and these curves are added we can apply a threshold to locate the edge. Mathematically, the component edges may be constructed as a series of orthogonal base functions under the applied weight function, which makes the decomposition into an explicit scalar product operation. Such base functions have been described in R. C. Y. Chin, "A domain decomposition method for generating orthogonal polynomials for a Gaussian weight on a finite interval" in Journal of Computational Physics, Volume 99, Issue 2, pp. 321-336 (1992).

In an example embodiment, the threshold value is determined statistically from a number of measurements. In a measurement situation, e.g. CD metrology, the threshold should be set at the physical edge position. This can be done by comparison to a reference structure gauged by a particle beam, a near-field probe, or a scatterometer. In mura detection, however, stability of detection is the most important characteristic. To improve the stability we recognize that the measured variance is the sum of the sample's variance. Since the sample's variance does not vary with the threshold setting, the threshold setting can be automatically optimized using the inverse of the measured variance as the merit function. A workpiece, or a part of it is measured and the variance is calculated for different settings of the detection parameters, e.g. the threshold setting. The procedure may be generalized to optimization or selection of edge component functions, the weight function, the choice of sub-windows (described below) and also the settings of the detection hardware, e.g. camera, focus, projection optics, illumination and scanning.

The described optimization is also useful for CD metrology if the hardware and edge location settings are optimized for minimum measured variance. The measured CD will then in the general case not be correct as shown by a difference between a measured CD value of a reference structure and its known value from independent measurements. The known difference may then be added as a correction. Furthermore corrections for different types of samples and features may be stored in a library for future use. It is an aspect of the technology disclosed that an optical system for measuring placement, size and shape of features may have a supplementary sensor with a near-field probe (e.g. AFM, STM, or SNOM probes) for calibration of line width, shape and edge profile. Said probe may be retracted during normal operation and brought forward for calibration or reference measurements. Small-footprint near-field scanning modules suitable to be used as an auxiliary calibration sensor are available commercially from several sources, e.g. from Danish Micro Engineering DME of Denmark.

If the (possibly modified as shown above) edge trace is monotonous and well-behaved the pixel values may be multiplied with the weight function, which may be the line spread function or an approximation of it, The weighted values are summed up and divided by the sum of the weights to produce a weighed edge intensity. This is compared to the pre-determined threshold and the difference is converted to an equivalent displacement for the edge inside the window. For small displacements a linear approximation of the edge transition may be used, or the actual function I(delta) where I is the computed weighed intensity and delta is the displacement relative to the nominal edge. The linear conversion factor is found as 1/(dI/ddelta), the inverse of the derivative for small displacements. For large computed displacements the determination is repeated with an adjusted nominal position as described above.

Figure 5A:
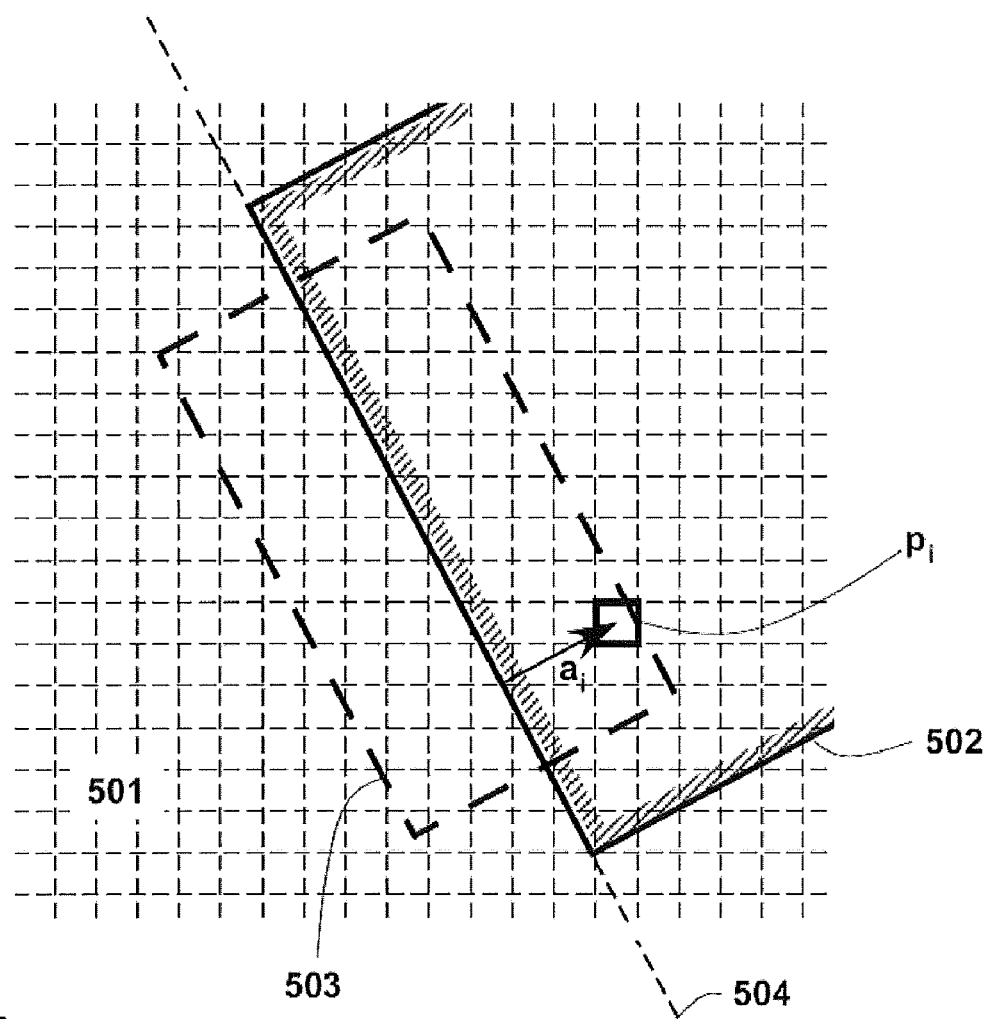
In FIG. 5a, a feature captured by the camera is shown. The measurement window is defined along a straight part of the edge and for each pixel within the window the intensity is plotted in FIG. 5b against the position perpendicular the edge. After the data has been cleaned from outliers a model for the edge is fitted and the position of the edge determined.
Figure 5B:
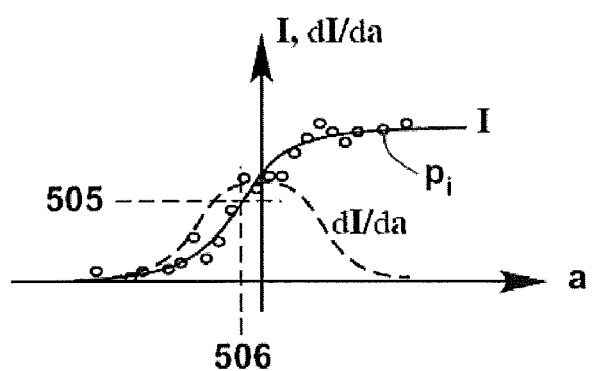
FIGS. 5c-d illustrate the notion of sub-windows.
FIGS. 5e-h illustrate examples of handling more complex edges in a unified way.
Figures 5C, 5D:
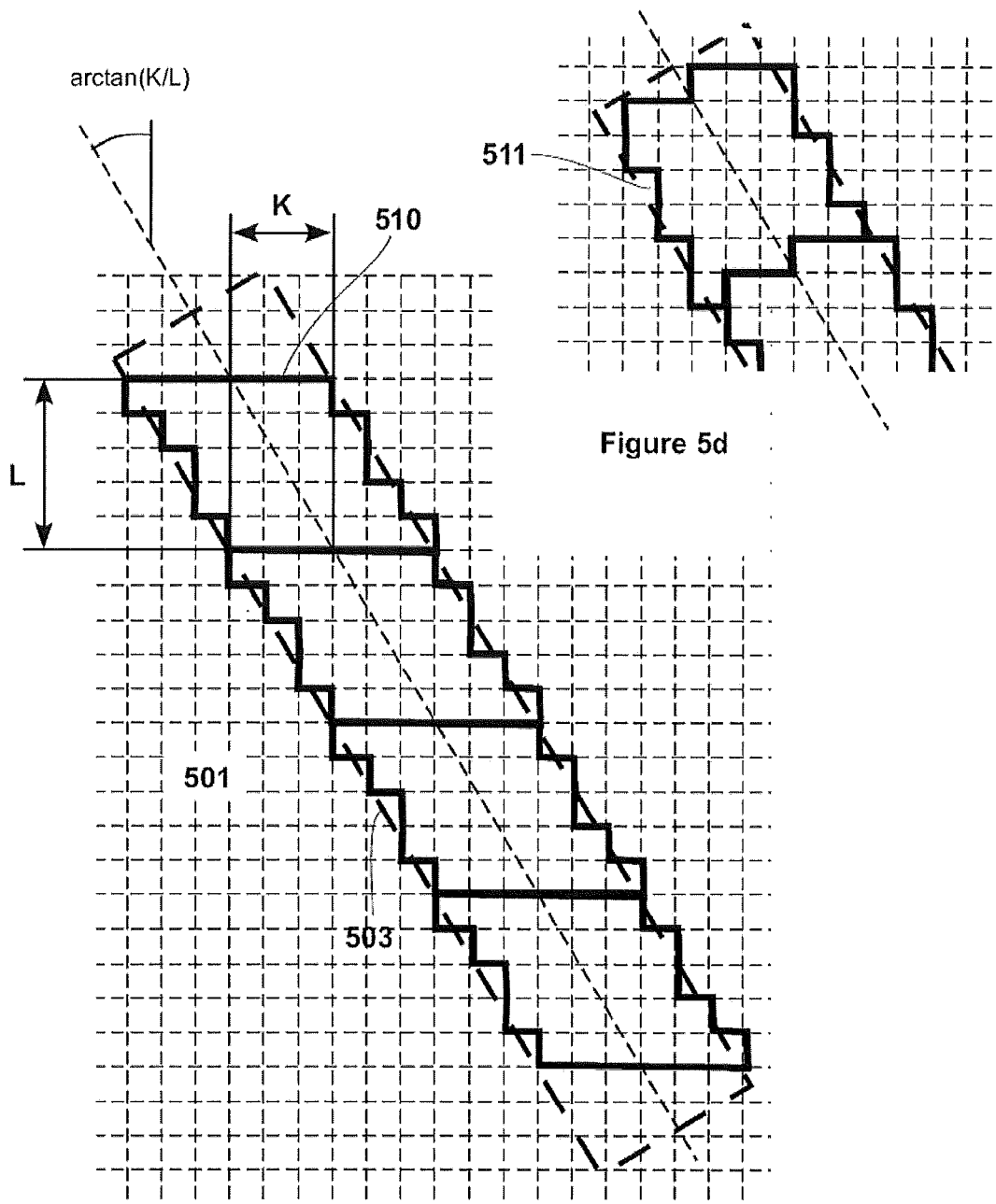
Figure 5E:
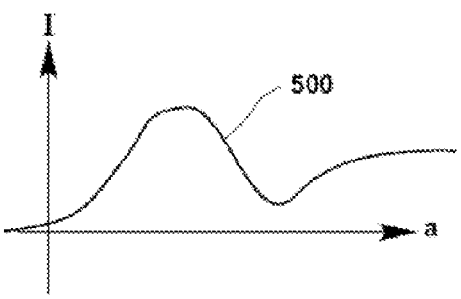
Figure 5F:
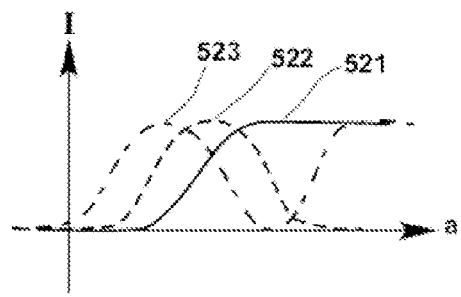
Figure 5G:
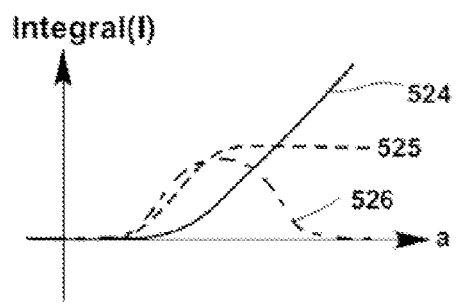
Figure 5H:
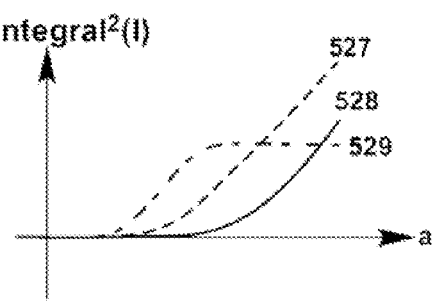
Figure 6:
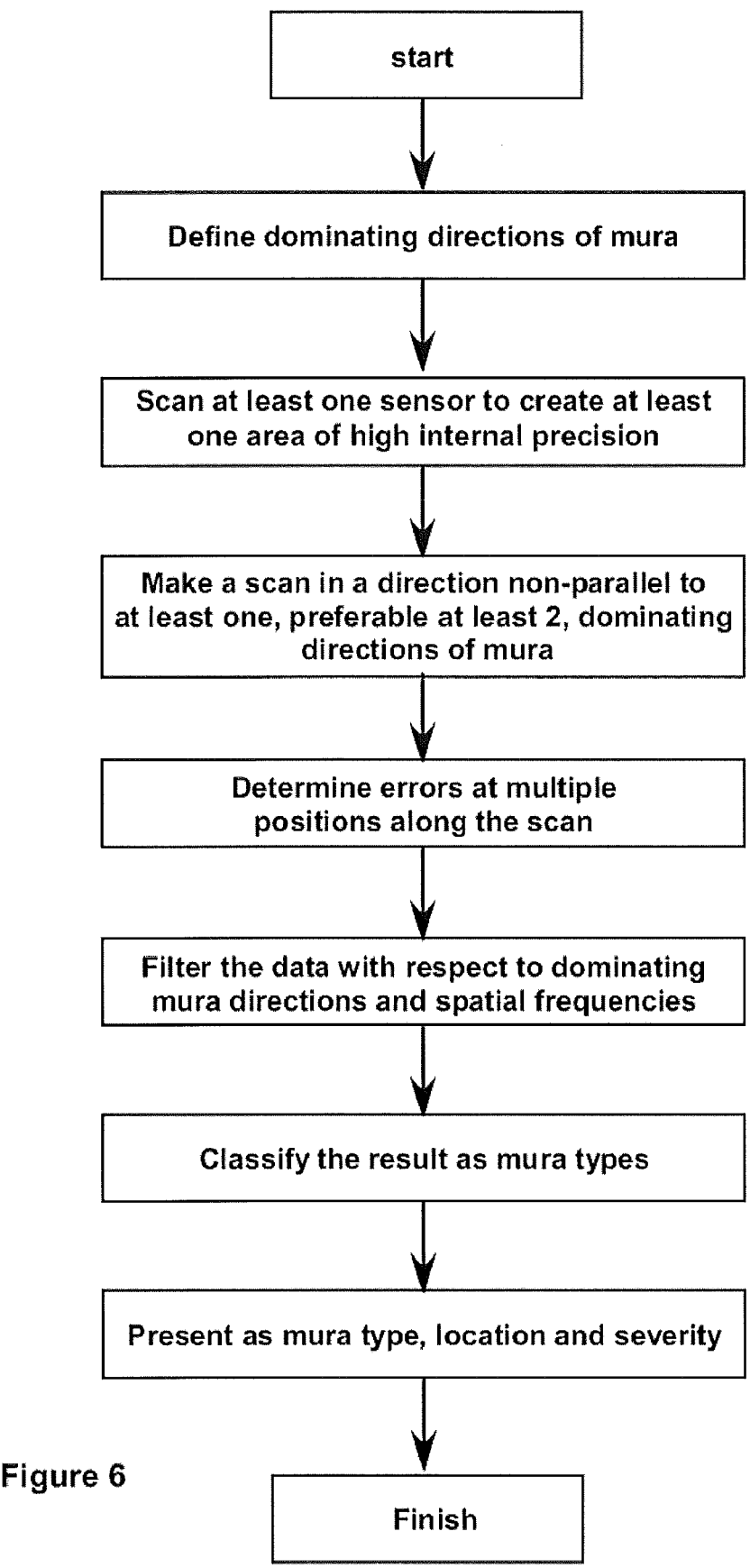
FIG. 6 shows a generic procedure for finding mura effects with a sensitivity higher than the stability of the metrology hardware.
Figure 7:
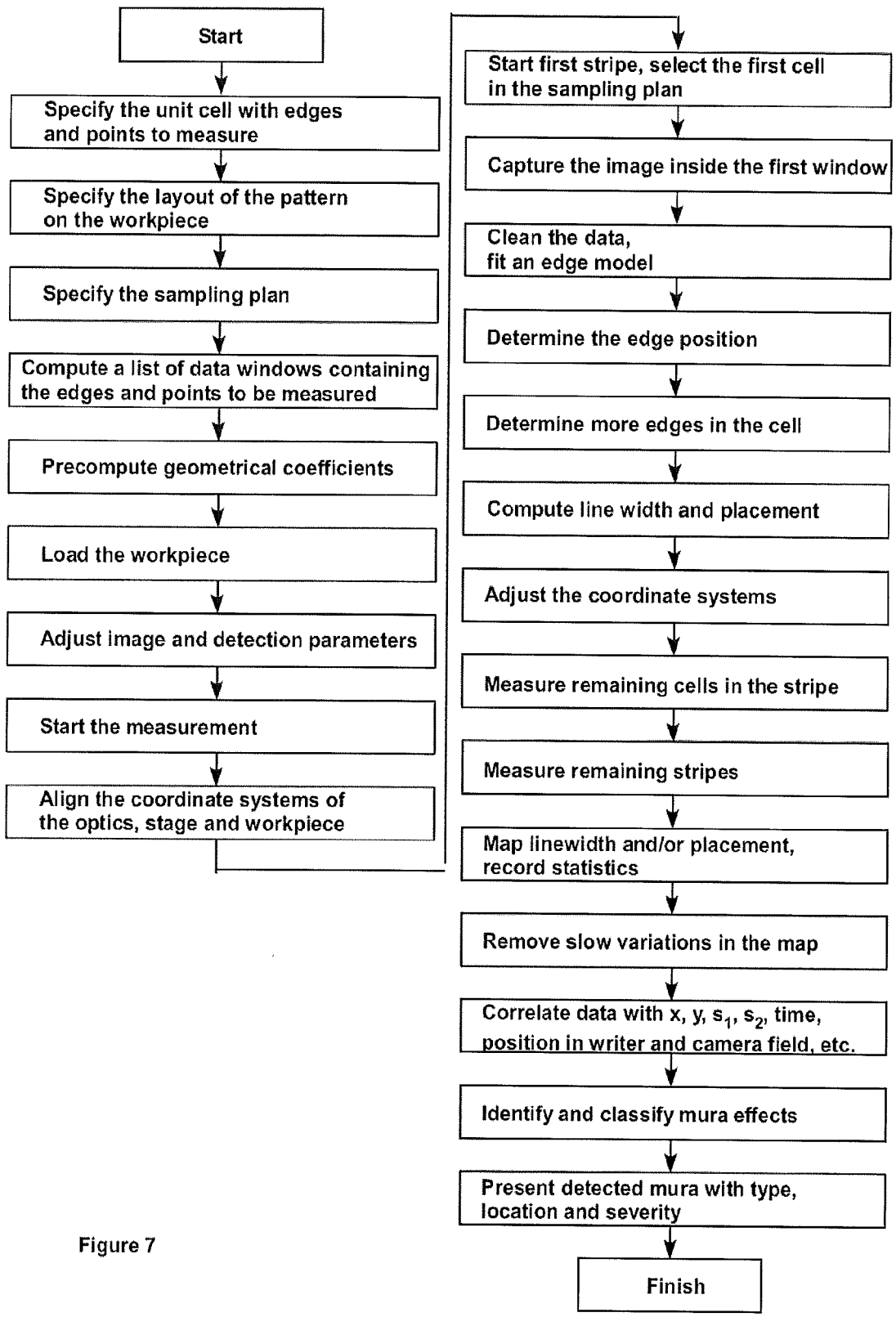
FIG. 7 shows a more detailed procedure for finding geometrical mura in a patterned workpiece.

The described algorithms work for any angle between the grid and the edge. Many patterns are Manhattan-like, i.e. the edges are parallel to the directions of repetition in the pattern. A specific angle may be chosen between the bitmap and the typical edges which makes the determination of these typical edges easier or more accurate. An example embodiment of the method has the rotation angle of the bitmap relative to the typical edges equal to arctan(K/L) where K and L are integers. The absolute value of K and L are less than the length of the window in pixels and typically less than 10, preferably less than or equal to 5. FIGS. 5c-d show K=3 and L=5. Setting the tangent of the angle equal to a rational number with small K and L makes the placement of the bitmap pixels relative to the edge repeat with a short period. The algorithm described above which multiplies every pixel value with a weight which depends on the distance to the edge will use a small number of values for the weight function repeated in a short sequence along the edge. In the example in 5c the weights are repeated for every 5 pixels in the vertical direction. If the edge is ideal, the measured values will also be repeated and if we determine the edge position for each 5 rows we will get a repeating result, including errors coming from the large truncation to the pixel grid. We call the repeating units 510 in the algorithm sub-windows. FIGS. 5c and 5d show that alternative definition of repeating sub-windows 510, 511 can be defined for the same edge. When the edge displacement is measured in a window 503, the window may be replaced by an integer number of sub-windows in order to remove randomness that comes from the position of the ends of the windows. A sub-window as defined here removes the through-grid dependence of the edge position. Each sub-window is a fixed cluster of pixels which sample the edge at a systematically distributed number of distances and gives a similar result as if the edge was parallel to the bitmap and highly oversampled. Furthermore, the use of computed weights that may take the geometry of the pixel into account, by computing super-sampled weights and integrating them over each pixel, makes the determination of the edge position highly linear.

The a priori knowledge that the sub-windows should measure identically can be used in a number of ways: If a window is 100 rows long and has 20 sub-windows and 2 sub-windows measure distinctly different one may conclude that there is dirt or some other disturbance and remove these sub-windows from the data. The standard deviation of the sub-windows may be used to quantify edge irregularity or roughness. Systematic bending in the edge may also be seen in the sub-window data.

The analysis with sub-windows may be driven one step further. If the average of the edge displacement is calculated from the first row in every sub-window and the same is done for rows 2, 3, 4, and 5 in the example in FIG. 5c, the five row averages will be different due to the positions of the pixels relative to the edge. The difference can be identified as a through-grid measurement artifact and be stored for future use. The measured single-row displacements may now be corrected for the row artifacts to remove the through-grid variation. This gives a fast row-by-row determination of the edge position that can be used for edge roughness analysis, i.e. spectral analysis.

Benefits of the angled measurement, and especially when using a rational number with small nominator and denominator as tangent of the angle, is that a pixel size much larger than is commonly used in metrology system can be used. In prior art images are typically oversampled so that at least 3 and often 5 pixels per FWHM are used in order to get a smooth image of the edges and no moiré effects between the camera and the pattern. With the methods of the technology disclosed, one pixel per FWHM can be used to measure straight edges with essentially no through-grid effects at all. In a particular embodiment it may be advantageous to decrease the size of the pixel somewhat, e.g. to get a smoother image to look at, to a value in the range 1-1.5 or even in the range 1.5-2 pixels per FWHM in the image. Since the speed of many quality-control systems are limited by the cost of handling and analyzing a high pixel flow this can be translated to three times higher optical resolution in an equivalent system. That said, it may be advantageous to use the described edge algorithm for any pixel size.

The other factor related to the speed of a real system is the cost of data processing where if each edge position must be established from many pixels, e.g. by model fitting, may be slow. We have described a method which needs essentially just one multiplication and addition per pixel in the window plus calculation or table look-up of the weights for the first sub-window in the window. Typically, we already know approximately where the edge is. The coordinate system is set up after an alignment procedure at the start of each scan line and from there on each edge will be very close to where it is assumed to be. Alignment errors and mechanical drift may cause the pattern to move with time or along the extended field. The expected edge positions can be updated with a rolling average or otherwise extrapolated placement correction based on the previous measurements. Accurate pre-alignment will speed the algorithm in finding the edge position without iterating and is only numerical. There is no need for real-time adjustments of the camera movement.

Analysis of the Data

Analysis of data will be described in an example embodiment detecting mura effects created by subtle placement errors in a large-area mask, since this is probably the most demanding application of the technology disclosed. The methods used for placement may be applied to other properties with little or modest modification. The word "placement" in this chapter can be read as synonymous to "measured property" or "property" and "camera" is synonymous to "sensor". For workpieces having other systematic error sources than maskwriter stripes the method can be adapted to account for these systematics.

The camera captures stripes of image data and the data is processed to extract x and y placement of the features designated for measurement in the sampling plan. The sampling plan can be more or less complex, e.g. with regular oblique scan lines or a hierarchy of nested groups of scan lines and in each line the may be and a regular or irregular sampling plan. Each feature is put into a database or table with a record containing several parameters: measured x and y placement errors, the nominal x and y placements, the placement in the coordinate system defined by the movement axes of the instrument, the number of the measure stripe and the coordinate inside this stripe, the number of the maskwriter stripe or field and the coordinate inside this stripe or field (based on a priori knowledge of the maskwriter job or extraction of the maskwriter parameters by analysis of residual field artifacts in the recorded image), the time of writing and the time-stamp of the measurement, focus sensor reading, air pressure, temperature and humidity at the moment of measuring, i.e. essentially any available information that the data may have a dependence on. Some of the information listed is redundant and may be coded differently and possibly more compact.

The analysis uses the different signatures to separate between mura effects, instrument artifacts, and pure noise. Different sampling plans have different ability to do so. The separation can be very strong if the signatures of the workpiece and the instrument are mathematically orthogonal, i.e. an analysis scheme where workpiece errors and instrument errors are calculated and an error in the workpiece does not produce a calculated instrument error, and vice versa.

Averaging over the unwanted input parameter suppresses it down to some cut-off spatial frequency which depends on the averaging length. For mura detection the long-range effects may not be relevant and may be removed from the result of the calculations, or alternatively filtered out from the measured data. This is equivalent to a high-pass filter with a certain cut-off spatial frequency. Averaging an unwanted parameter over a distance larger than one period of the cut-off frequency will strongly suppress the unwanted parameter. A simple way to average out an instrument axis is to tilt it relative to the axis of the dominating axis of mura, or to make it curved. The suppression of the axis may be further improved by application of a weight function. This is equivalent to apodization in signal processing, and one such useful weight function is a Gaussian bell curve. The formula for finding the dependence on x and suppressing all other input parameters is then to integrate the placement error e times the weight was a function of x and do the integration over all other parameters.

Figure 12:
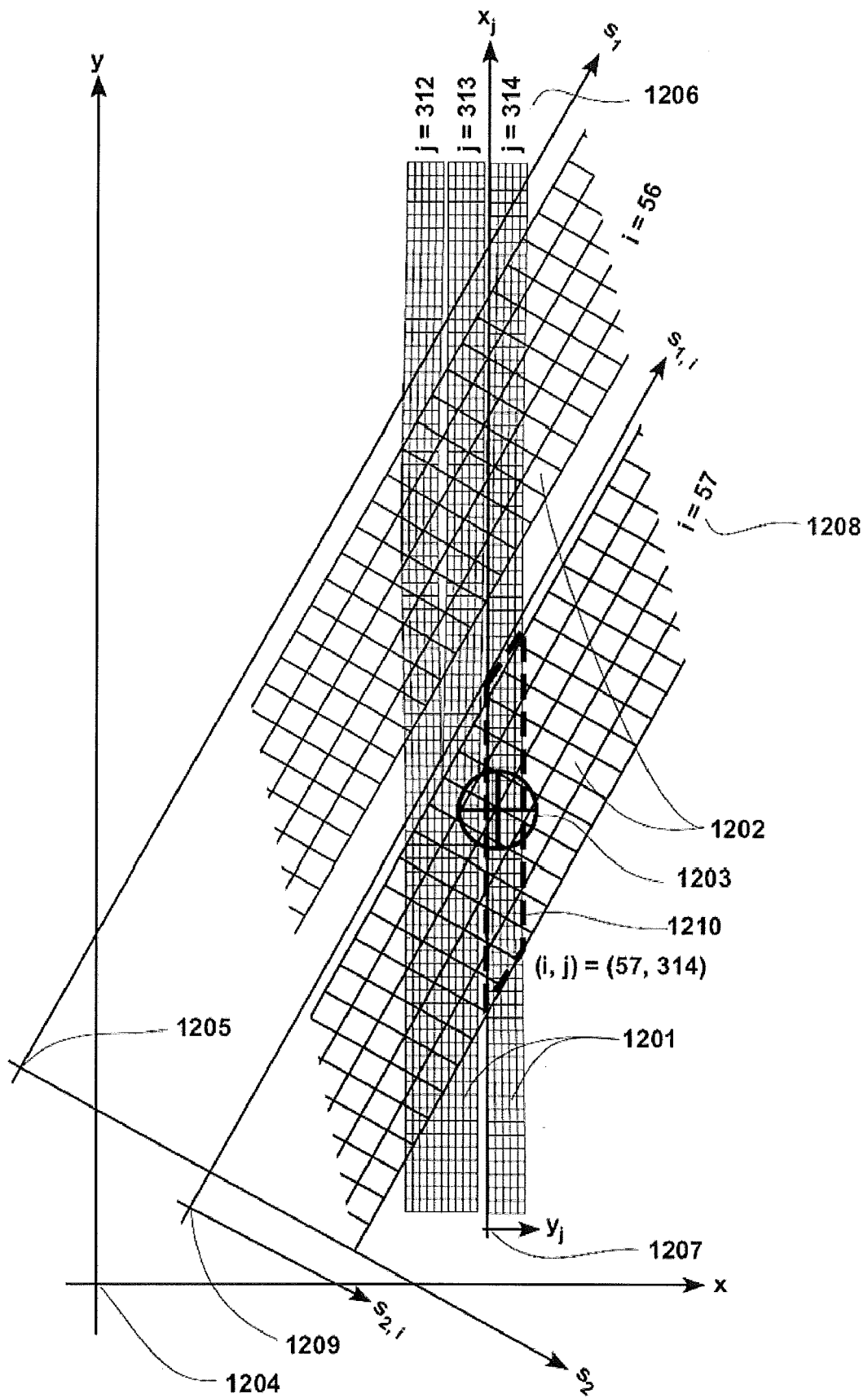
FIG. 12 shows coordinate systems useful for the analysis of data

FIG. 12 shows as an example some of the input parameters which can be used to separate the mura from noise and instrument errors in a mask. The figure shows a pattern written as stripes 1201 by a maskwriter and measured in parallel (but not accurately parallel) stripes 1202. The circled cross 1203 is one measured point, e.g. the x placement error of a feature $e_x$. The mask has the coordinate system 1204 with the axes x and y. In the example x and y are dominating directions of mura. The measurement system has the coordinate system 1205 with the axes $s_1$ and $s_2$, which are the axes of the sensor movements, e.g. $s_1$ is the linear scanning along a beam and $s_2$ is the repositioning of the workpiece between the measure scans. Distortions in the workpiece make ex depend on x and y and errors in the instrument makes it depend on $s_1$ and $s_2$, i.e. $e_x$ can be modelled as $$e_x = e_x(x,y,s_1,s_2) + e_{x,non-modelled}.$$

The maskwriter stripes are denoted by j and each stripe has a random placement error. Likewise the measurement stripes are denoted i and also have some random placement error. In the example the measurement 1203 belongs to the writer stripe 1206 with j=314 and to the measure stripe 1207 with i=57. Now we have $$e_x = e_x(x,y,s_1,s_2,i,j) + e_{x,non-modelled}.$$

Furthermore the writer stripe 1206 has an internal coordinate system 1207 with the axes $x_j$ and $y_j$, i.e. $x_{314}$ and $y_{314}$. The measure stripe has the axes $s_{1,i}$ and $s_{2,i}$, i.e. $s_{1,57}$ and $s_{2,57}$. We now know that $$e_x = e_x(x,y,s_1,s_2,i,j,x_j,y_j,s_{1,i},s_{2,i}) + e_{x,non-modelled}.$$

The modelled part of the error $$e_{x,modelled} = e_x(x,y,s_1,s_2,j,x_j,y_j,s_{1,i},s_{2,i})$$

can be determined from the local measurements.

It may be practical to limit $e_x(x, y, s_1, s_2)$ to frequencies that are not sensitive to mura. Then $e_x(x, y, s_1, s_2)$ will swallow long range workpiece distortions and drifts in the stage system and sensor which are typically not important in mura detection. The mura is then found by analysis of $e_x(j)$ and $e_{x,non-modelled}$, assuming that writer stripes play a dominating role in the mura creation. It is useful to separate the errors related to the stripes (or generalized: related to the systematics of the pattern exposure or creation) and errors that are independent of the stripes. Local stripe displacements $e_x(j)$, will give mura if the displacement of a single stripe is above some limit or if over successive stripes an accumulated average error becomes visible. This can be modelled by filtering by the subjective contrast sensitivity of the eye and thresholding the result. A numerical mura index may be produced by integration over all spectral frequencies weighed by the spectral contrast sensitivity function of the eye. This can be done globally or region by region on the workpiece. What will be described below is a frequency analysis and this can be done on patches defined by a windowed function or alternatively a wavelet analysis yield a spatially resolved frequency analysis.

Figure 14A:
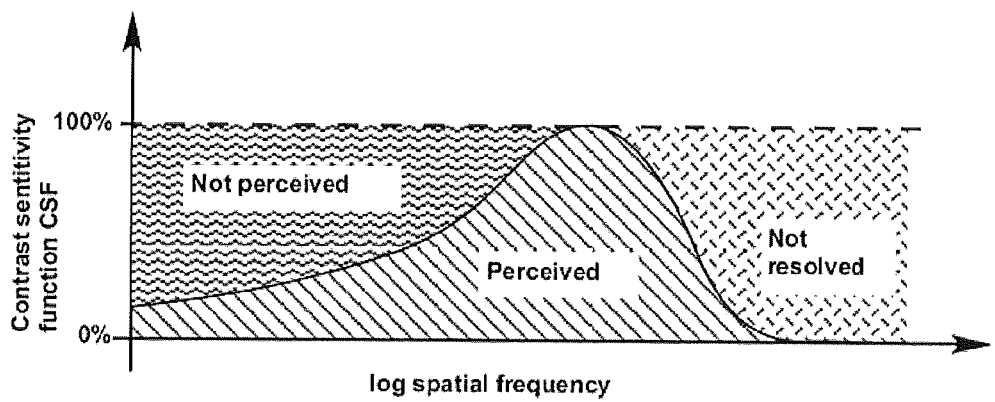
FIGS. 14a, 14b, 14c give a conceptual view of how mura errors are separated from drift, distortion and noise.
Figure 14B:
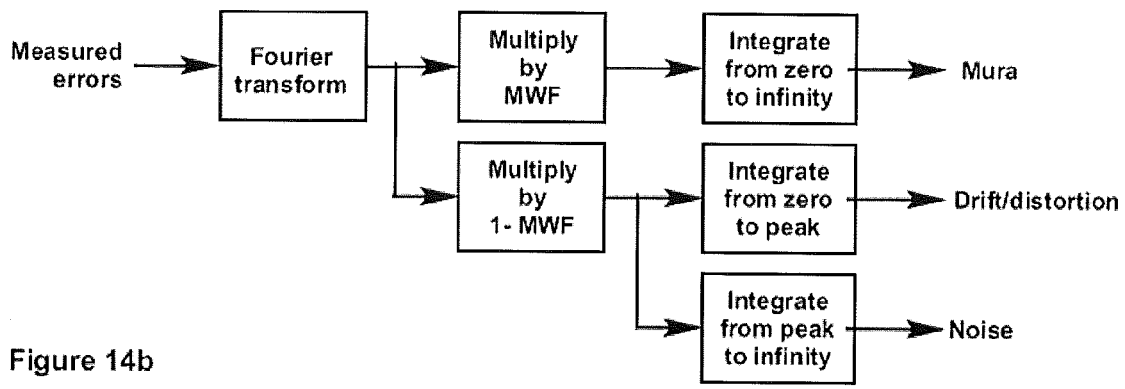

The contrast sensitivity function CSF conceptually shown in FIG. 14a is the visual contrast perception function found in many textbooks and papers (e.g. P. G. J. Barten, "Contrast sensitivity of the human eye and its effects on image quality", SPIE, Bellingham, 1999), normalized to 100% at the peak. The peak is at approximately 2 periods per degree visual angle. Therefore the horizontal axis scales with the viewing distance. At three meter viewing distance the peak is at one cycle per 25 mm. FIG. 14b shows how the contrast visibility function can be used as a weight function (the mura weight function MWF) when integrating the errors to produce an integrated mura content. Errors that do not go into mura may be collected into noise and drift/distortion.

Figure 14C:
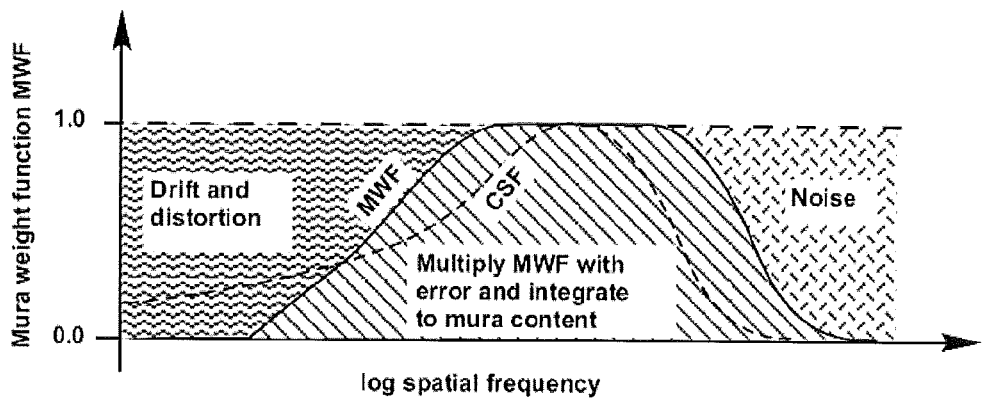

While FIGS. 14a-b show the principle, FIG. 14c shows a better mura weight function or MWF. Since the viewing distance when the display is used—and when its quality is assessed during manufacturing and at the point of sale—is unknown the peak of the contrast sensitivity function has been stretched to include a range of frequencies at the highest sensitivity, producing a more conservative weight function. The range at the peak may in an example case be ½ per mm to ¹/₅₀ per mm corresponding to a range of viewing distances from 200 to 6000 mm. Instrument limitations may limit the availability or precision of data for low spatial frequencies, and therefore the weight function is set to go to zero below some imposed low-end cut-off. Methods to extend the range of high internal precision will be described below, and with these methods some of the unaccounted-for low-end mura in FIG. 14c can be recovered. The MWF in FIG. 14c gives a conservative mura index, which will in most cases overestimate the mura within the specified viewing range, but never underestimate it.

The non-modelled error may be treated in a similar fashion. In two dimensions the WMF may be anisotropic, i.e. being different in different directions. This preserves signal-to-noise in situations where the hardware and the method to use it has different lengths of high internal precision in different direction. The frequency analysis as described above may yield the magnitude and frequencies of errors, and it will also quantify random errors within the sensitive frequency bands. This is not the same as what we have called noise above: the frequency analysis quantifies noise as non-resolved high-frequency errors. Excessive random variation may signal random fluctuations in the pattern, e.g. etching problems which may give rise to visible mura, but in a sparse sampling plan it may also signal a systematic variation which is under-sampled. Typically, an area with high random variation should lead to further analysis, e.g. rescanning in stitching mode described further down. Alternatively, or as a complement, methods of multiresolution analysis discussed in many textbooks (e.g. Multiresolution Signal Decomposition: Transforms, Subbands, Wavelets by Ali N. Akansu and Paul R. Haddad) may be used to find systematics in the random-like data.

CD and Placement Mura Detection Apparatus

The following is a description of a preferred embodiment for measuring mura effects in photomasks. The embodiments described can be modified to measure smaller or larger workpieces. The embodiments described also can be adapted to increase the resolution to measure photomasks for image sensors or memories by using shorter wavelength, higher NA, immersion, optical and numerical image enhancement, super resolution, etc. The immersion can be in the form a liquid, e.g. water, water with salts, oil, fluorinated alcohols, or any other liquid providing a suitable combination of index and compatibility with the measurement and the workpiece. Alternatively solid immersion may be used where a prism or lens made from a high-index solid material, e.g. glass, diamond, garnet, sapphire, metal oxide, etc. is placed close enough to the workpiece so that there is no gap between the workpiece and the lens/prism or so that evanescent wave can "tunnel" across.

One preferred system for measuring mura on photomasks has a stage taking substrates of 1600×2000 mm. The stage moves the substrate in one direction, corresponding to x in FIGS. 3a and 3c. Above the substrate is a beam 210 made from ceramic material and mounted an oblique angle from the y direction, and this angle may be about 28 degrees. Other fixed angles can be used, the angle may be variable as in 2 FIGS. 2a, 2b, 2c, 2d, 2e and 2f, or there may be two or more cameras on beams with different angles as in FIG. 2e. The camera unit 212 is mounted on a carriage 211 which slides along the beam on porous air bearing pads 216 which may be approximately 100 mm long. Smaller pads may be used, which produces a more uneven movement, the effect of which can be removed by calibration. The carriage is driven by a linear electric motor on the carriage. Other alternatives for driving a mechanical motion abound in literature: the carriage may be pulled or pushed by cords, bands, or rods driven by a remote motor, driven by a lead screw, having friction drive, etc. A specifically smooth drive is to tilt the beam (and the stage) and use gravity with a pneumatic or electromagnetic brake having a velocity-dependent braking force, e.g. a copper sheet in a strong magnetic field, e.g. an from an electromagnet. The distance encoder 204 is used as the master clock for the data capture and the speed is allowed to vary slightly as long as it is smooth.

Figure 8:
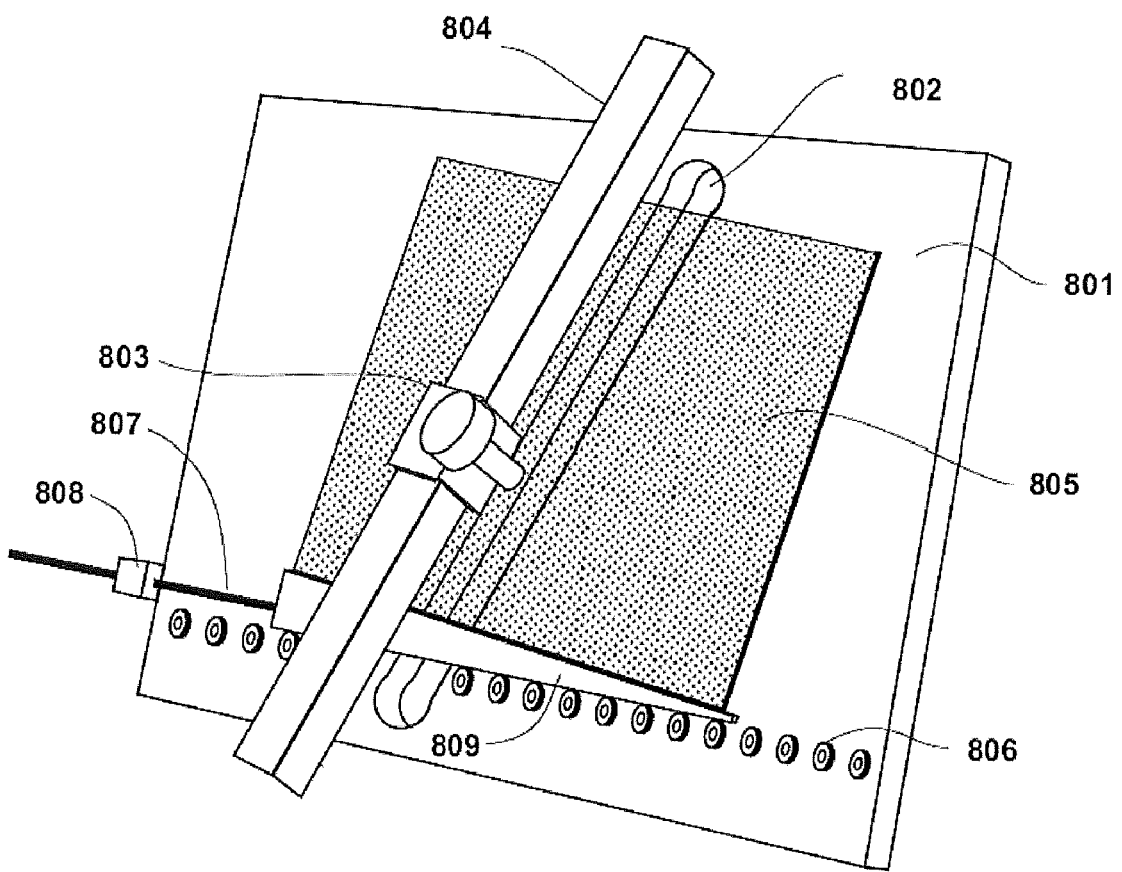
FIG. 8 shows an embodiment with a near-vertical stage and a slot behind the camera path.

The accuracy of the placement of the workpiece is non-critical since the operation is independent on accurate knowledge of the placement of the scan stripes. In a preferred embodiment the workpiece is clamped by vacuum during scanning, then lifted on air between the scan operations and moved on the stage. The surface in FIG. 8 on which the glass is placed has a slot along path of the camera on the beam. The reason for this is two-fold; first it makes it possible to use transmitted light with an illuminator tracking the camera for the other side of the workpiece. Secondly, leaving a stripe of the glass where it is measured to be suspended only by itself assures that distortion does not introduce high spatial frequencies due to the local clamping or unevenness in the glass surfaces. This is shown in FIG. 8. The stage 801 has a slot 802 below the camera 803 path along the beam 804. The workpiece 805 is clamped by gravity and moves on a row of rollers 806 driven by a push rod 807 driven by a mechanical motor 808. The wedge 809 makes the s2 axis of the instrument non-parallel to the x axis of the workpiece. FIG. 8 illustrates a preferred embodiment built to have the workpiece in a vertical or near vertical position. Other example embodiments have the workpiece horizontal or near-horizontal, or vertical.

Isolation from vibrations and acoustic waves at the level a few nanometers is not trivial. The stage may be supported by passive, or optionally active, vibration isolators and enclosed in a sound-reducing enclosure. Active sound compensation i.e. loudspeakers driven to null the incoming sound pressure, may be used to reduce the amplitude of infrasound. The stage is stiff with a high resonance frequency and high damping of the resonance. The beam is also designed to have high resonance frequencies and these higher frequencies are damped by internal friction e.g. by viscous material inserted in the mechanical system. The bending mode may be actively silenced, i.e. by an excitation opposite to the force that excites the mode. Remaining movements of the stage and the beam may be recorded by accelerometers and corrected for in the analysis of the data. In particular there may be accelerometers at each end of the beam and other ones in the middle. Other accelerometers or position encoders may be present in the stage on which the workpiece is resting. That way the relative movements of the camera and the workpiece may be recorded and used to correct the data during analysis.

The carriage 211 may carry the entire optical head 212, but it is advantageous to have a slave carriage 214 for carrying cables and electronics. The slave carriage may slide along a secondary beam 215. The illumination light can be transported to the camera in a fiber bundle or it can be generated locally by lamps, LEDs or lasers an illumination unit 213, which may be located on the slave carriage. If transmitted light is used a second slave carriage on the other side of the workpiece carries the illuminator. Having a slave carriage sliding along a separate beam makes it possible to lift of the weight off the weight of the camera by applying a force between the slave and the camera carriages. It may lift off the weight of the beam reducing or removing the gravitational sag of the beam. The force can be applied by magnetic, electromagnetic, mechanical or pneumatic actuators or by springs. It is also useful to use lateral forces between the beam and the secondary beam to dampen vibrations in the beam. The damping can be passive, e.g. by a squeeze-film between surfaces of the beams, or the vibrations may be measured and actively cancelled. Using the secondary beam to lift off the weight of the camera carriage and the beam itself and to dampen vibrations makes it possible to have a very long beam. Such a long beam makes it possible to rotate the glass relative to the beam as shown in FIGS. 2a, 2b, 2c, 2d, 2e and 2f. Rotating either the glass or the beam to different angles makes the system more flexible and may also be used for long-range measurements, even placement metrology over the entire workpiece as will be described below.

FIG. 2f shows in a conceptual way an example embodiment of the beam system. The main carriage 211 carries the sensor 212 above the workpiece 220 and slides along the precision beam 210 on long air bearing pads 216. An auxiliary beam 215 carries a slave carriage 214 which carries those parts of the sensor 213 which create heat or vibrations or just weight, e.g. illuminator, cables, motors, cooling, etc. The main carriage 211 has six accelerometers 217 which measure acceleration, velocity or displacement along up to six vectors, giving the translation and rotations of the main carriage 211. The measured movements are recorded, combined with similar movement measurements on the stage, and used to correct the measured data.

The beams in the example embodiment are made from alumina ceramics with polished surfaces. The sag of the precision beam due to the weight of the beam is removed by an upwards force on the beam from a sag-cancellation subsystem, in the example embodiment coming from a lift beam 221 inside the precision beam 210. The lift beam need not be straight and the lifting force at the center is adjusted by manipulating of the ends for more or less bending of the lift beam. The gravitational pull on the main carriage is cancelled by a force between the main carriage and the auxiliary beam, in the example embodiment a low-spring-constant mechanical spring 218. Higher-order vibration modes in the carriages and beams are damped by energy-dissipating connections between parts vibrating with different amplitudes, most importantly between the beams, in the example embodiment by an air squeeze film 219 between the carriages and a liquid film 222 between the precision beam 210 and the lift beam 221.

The beam system described above has been shown in the context of placement metrology or more generally of carrying a sensor, but may also be used also for writing or patterning systems. The benefit of the beam system is that the precision beam may be made significantly longer with a given cross-section than previously known beam designs and that the system offers very smooth operation and also very tight placement control if the measured movements are used to correct the recorded measurements or the placement of the written pattern. The beam system is described by means of example and details in the implementation of the principle may change depending on the actual requirements in the specific application.

The camera optics has an NA of 0.35 and incident (reflected) broadband white visible illumination with sigma larger than 0.6 and preferably about 1.0. Filters can be placed in the illumination path to change the angular distribution and spectral content of the light. With this large sigma (small spatial coherence) the image has little coherent fringe effects and the FWHM of the point spread function is around 0.7 microns. Alternatively the workpiece can be illuminated by transmitted light. The optics is telecentric on the object side. The camera head has an autofocus system based on a pneumatic flow sensor.

The field may 2048 camera pixels and each pixel is 0.7 microns in the object space, i.e. the stripes are 1.4 mm wide. The camera has a 2048 pixels×96 stages TDI sensor from Dalsa, a Canadian corporation, with 10×10 square pixels and 67 kHz line rate. The magnification of the optics is 14× and the scan speed 67 k×0.7 microns=46 mm/s. That means that the extended camera field is a strip 1.4 mm wide from side to side of the workpiece, i.e. 1.4×1700 mm and it is scanned in 45 seconds including mechanical overhead. The stripes can be scanned alternatively forward and backward. The data rate is 67 kHz×2048 pixels=140 Mp/s and each pixel is represented by 10 bits. The described apparatus is targeted for mura inspection of masks. For mura inspection of color filters and transistor arrays the pixel can be larges and the speed will be higher, e.g. 1.5 microns pixels for transistor array analysis will make the system run 4.5 times faster for a given pixel flow rate.

It is possible to build faster apparatuses. TDI cameras with wider field exist, e.g. a four times faster TDI sensor with 8096×96 pixel and 67 kHz line rate from Dalsa. It is also possible to use several cameras in the same apparatus. A faster example embodiment may have 10 camera units each with a sensor 8096 pixels wide from DALSA will scan 40 times more area per second.

Two other TDI sensors that may be considered are manufactured by Fairchild Imaging, model CCD 21241 and by Hamamatsu Photonics, model S10200. It is expected that all three sources mentioned for TDI sensors will introduce new models and continue to improve on their sensor design in ways compatible with the disclosed technology.

The data from the camera is captured on a computer running software for controlling, calibrating, and synchronizing the stage and camera hardware, conditioning the data, and performing analysis of the data to find and present mura effects. The image processing can be done entirely in software on a general-purpose computer, it may use hardware acceleration, e.g. with FPGAs available from Xilinx, Altera, and other companies, or it may be built with commercial GPUs (graphic processing units from ATI, nVidia or other companies).

Extending the Size of the Area of High Internal Precision

The camera and movement system has an area of high internal precision which is one measure stripe wide and a longer distance along the stripe. The relative precision between two points degrades with the distance between the points. An example embodiment has 30 nm relative placement precision or better over a distance of 30 mm, a second example embodiment has 10 nm over a distance of 100 mm. The precision between stripes may be significantly worse, partly because of the repositioning across the direction of the stripe, partly because of the time lapse between the recording of the two stripes. The visual sensitivity to mura is higher for short distances and gradually lower for longer distances. For pure mura detection the data may be filtered with a band-pass filter, e.g. having a pass-band in displays with a low cut-off at 3 periods per millimeter and a high cut-off at 1/500 millimeter. This range encompasses frequencies that are sensitive in computer monitors and small displays as well as in TVs. For TVs the pass-band may be changed to ½ per millimeter to 1/200 millimeters or for large screens 1/5 millimeters to 1/500 millimeters. These pass-bands are given as examples and the pass-band may have cut-off frequencies between these values. For image sensors and devices to be used for projection display the frequencies may be scaled according to viewing angle. Furthermore the data may be filtered by a filter which models the visual system at the distance or magnification the display or sensor is intended to be used. The high sensitivity to errors over relatively small distances fits well with hardware which has extremely high relative accuracy or precision over small distances, but looses some of the precision over larger distances.

It may still be useful to extend the range of high internal precision. Making the system accurate over larger distances may be useful for quality control other than mura detection and it may provide cleaner data and better diagnostics. The long-range accuracy may be improved in several ways and different methods may make the precision more isotropic in the short range or it may extend the precision to the entire workpiece.

A first example embodiment uses the precision of the pattern itself to provide a ruler over larger distances. A modern maskwriter for LCD-masks may have a registration accuracy of 100-200 nm (3 sigma). The mask pattern may further be measured in a coordinate system with an accuracy of better than 100 nm. This a priori knowledge can be used to calibrate the long-range coordinate system of the mura detection tool. High-frequency variations are measured to better than 10 nm, a precision which degrades over longer distances but not below 100-200 nm 3 sigma which is the accuracy of the pattern. This fits with mura requirements of higher short-range precision and relaxed precision over longer distances. A mathematical way to do this synchronization of the measurement to the pattern is to map the measured placement error across the workpiece, then low-pass filter the errors and subtract them from the measurement data. The result is a new set of measured data which has no long-range errors. The long-range accuracy of the measured data is that of the pattern which was measured.

Another example embodiment increases the area of high internal precision by measuring a first set of stripes with one direction, then measuring a second set of stripes with a second direction across them. The two crossing sets of stripes will allow an accurate determination of the relative placement of the stripes in each set and extend the area of high internal precision to an area which is spanned by the areas of high internal precision in each direction. If they cross at a right angle the area of high internal precision will be a circle with, in one example embodiment, 30 nm precision within a diameter of 30 mm and, in another example embodiment, 10 nm precision within a diameter of 100 mm. The crossing sets of measured stripes can be taken by two movement, e.g. stage and sensor, by two one-dimensionally scanning sensors or by one sensor scanning in two direction, e.g. by rotation of the workpiece or by rotation of the beam.

Figure 9A:
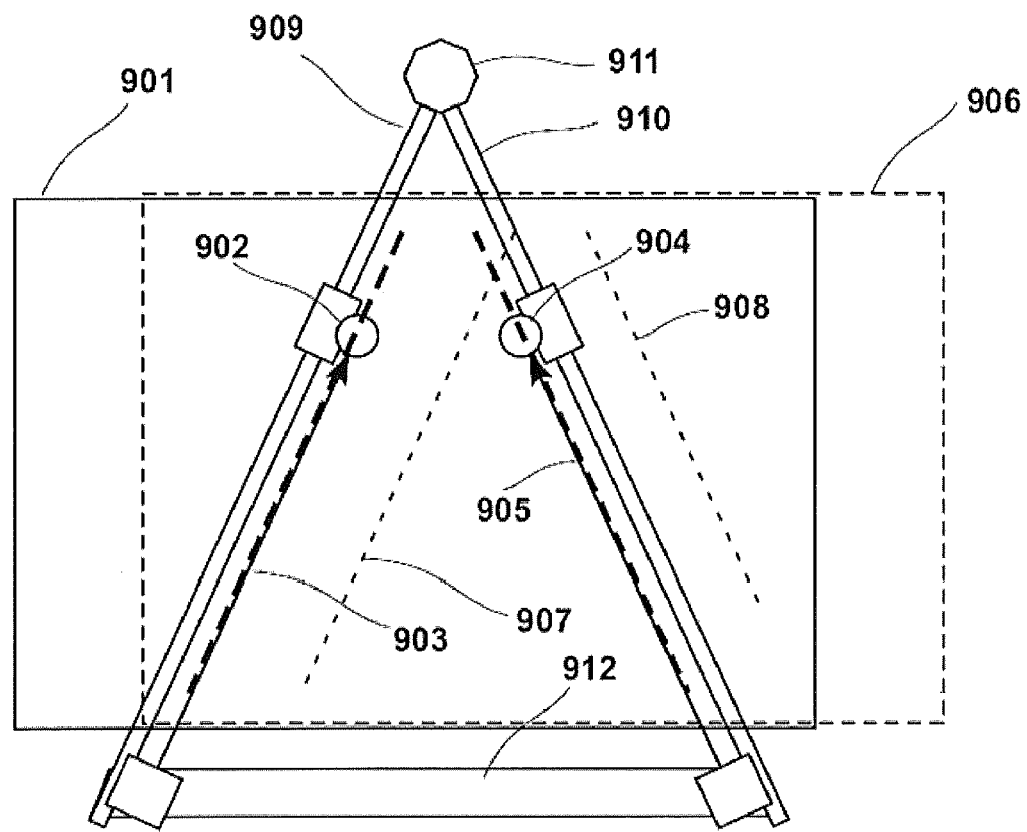
FIGS. 9a, 9b, 9c, 9d, 9e and 9f show how the long-range accuracy may be increased. These figures show conceptually the path of a sensor with drift as it is scanned by a two-dimensional scanning system (e.g., by a gantry system or by moving carriage and workpiece simultaneously) in order to produce areas of high internal precision also across the individual scan lines.

FIG. 9a shows an example embodiment with additional features to improve the long-rang spatial accuracy across the stripes without rotating the workpiece. The apparatus in FIG. 9a may be used to measure the registration, i.e. the placement accuracy over the entire surface, of a workpiece passing the apparatus on a conveyor. The workpiece 901 to be measured is placed on a surface and held still, e.g. resting on a flat surface by gravity, and two cameras 902, 904 are scanning the pattern and extracting the placements and the edges. The two cameras scan along two beams 909, 910 and form two extended camera fields 903, 905 that are essentially linear, but with an angle between them. At least one of the beams may be non-parallel to the axes of the workpiece. At least one of the beams may also be non-parallel and non-orthogonal to the direction by which the workpiece is moved between measurements. The shape of the beams is known and any divergences from straightness and are assumed to be known. The scale along each beam is likewise known to the target accuracy that is intended for the 2D measurement. It may typically have a laser interferometer with wavelength control from comparison to an etalon or from atmospheric data. It may be useful to have a reference for absolute length or absolute wavelength in the system, e.g. a known ruler or a known etalon or other wavelength reference. After the workpiece has been scanned in one position 906 giving two scan lines 907, 908 it is moved to a new position 901 and scanned again giving two more scan lines 903, 905. The relative distortion within each extended field is accurately known, but the placement of the fields relative to the workpiece is uncertain.

Figure 9B:
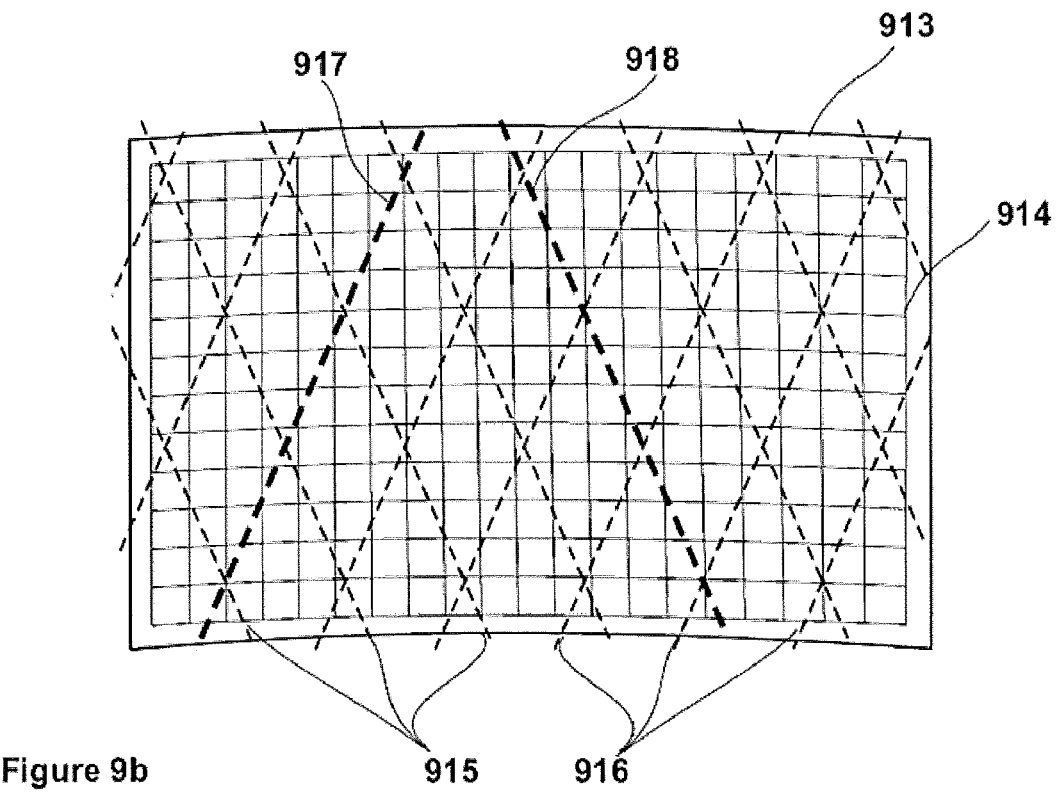

After the workpiece 913 has been stepped and scanned a number of times, giving a criss-cross pattern, FIG. 9b, of extended fields 915, 916, it is possible to calculate the placements of all scan lines (extended fields). Each scan line is assumed to have a placement and an angle relative to the workpiece. Then the measurement results that would result from these assumptions are calculated and compared to the actual measured data. The assumptions are adjusted for a better fit until the fit is optimized, e.g. in a least square or a maximum likelihood sense. The relative placements of the lines are then known.

It is necessary to have a known relation between at least one position of one camera and another position on the other camera, for the solution to be unique. In the example embodiment there is a known relation between the scan lines 917, 918 taken simultaneously by the two cameras. In the example embodiment in FIG. 9a this is done by connecting the two beams 909, 910 by a stable structure 911 and 912 into a fixed triangle. By doing so, and using the known relation in the fitting of the data described above, it is possible to measure the x-y placement of the entire area of the workpiece without having an accurate 2D (xy) stage. One may think of a large 2D interferometer-controlled stage being replaced by the stable triangle which is much simpler. The theoretical accuracy of the 2D coordinate system created by the mathematical fitting of the placement of the glass relative to the triangle during each step is of the same order as the stability of the triangle and the measurement noise i.e. a few nanometers. In practice it may be limited by the clamping distortion of the workpiece.

The procedure uses the relative movement of the triangle and the workpiece and it may be advantageous to have a fixed workpiece and a moving triangle. A typical large-area 2D metrology system, with a camera or sensor moving along the short axis of the workpiece and the workpiece moving in a perpendicular direction, would if built for a generation-10 LCD mother glass (approximately 2600×3000 mm) be 2.6 by 6 meters plus enclosure, and would need a 2.6 by 3 meter interferometer-controlled moving stage. Built according to this embodiment, it would have a 3 by 3 flat passive surface where the glass would sit. The triangle with the cameras could be kinematically supported and stepping along the workpiece, having interferometric high-precision movements along the beams. The movement of the triangle itself may be built with less precision e.g. simpler laser interferometers or optical or magnetic encoders.

In a different example embodiment a beam with a sliding camera is mounted on a precision (e.g. interferometer-controlled) xy stage giving a full registration metrology system. Such a system may be built on the same principles as the Micronic MMS1500 metrology system: extremely tight climate control, precision interferometers using a weather station and a $CO_2$ gauge to calculate the wavelength by an improved version of the Edlén formula. The absolute length scale is established by a ruler with fiducials made from low-expansion and low-aging material. The combination of using self-consistency and very accurate one-dimensional measurements with a precision two-dimensional stage may increase precision and make calibration of the stage more efficient.

Figure 9C:
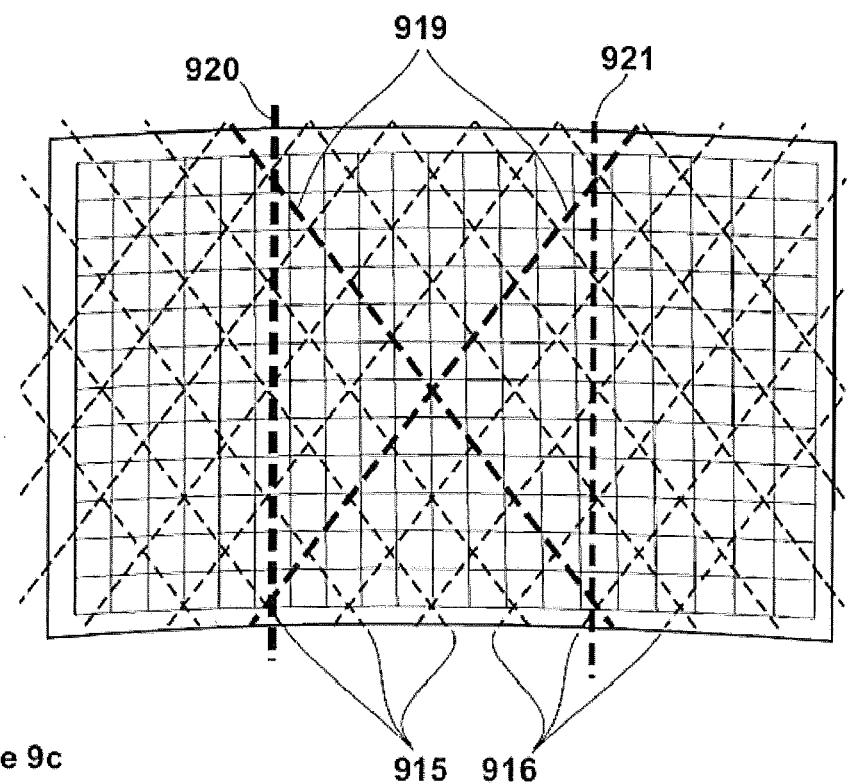
Figure 9D:
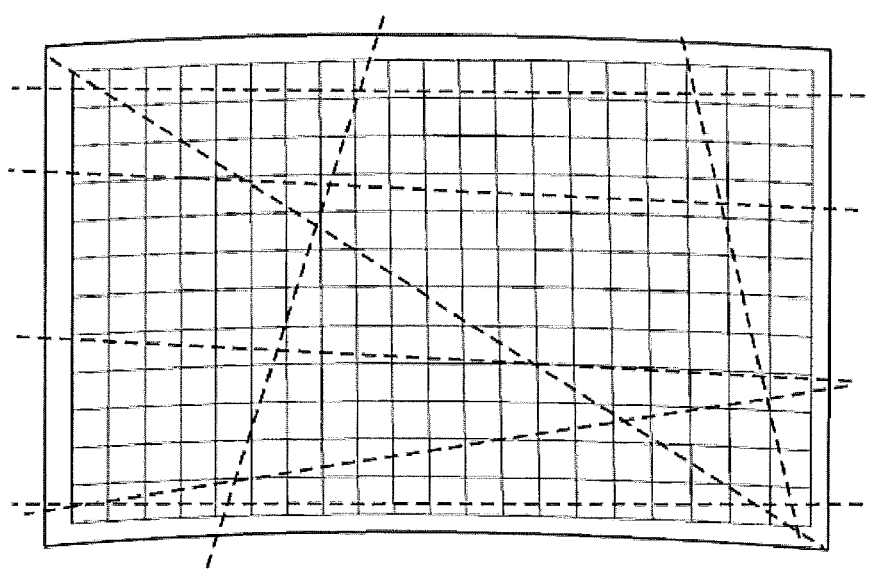

The rationale for the fixed triangle in FIG. 9a-b is to determine the orthogonality error of the pattern. If the workpiece can be measured by a straight ruler along three mutually crossing lines the orthogonality may be calculated by triangulation, FIG. 9c. Two sets of lines 915, 916 are measured and provide a coordinate system with high accuracy but with an unknown orthogonality error. A line 920 which forms a triangle with two lines 919 at two different angles can be used to calculate the orthogonality. One or more additional lines 921 will provide redundancy and better accuracy. The scheme can be generalized to multiple lines at multiple angles with at least three lines forming a triangle, FIG. 9d. Knowing that each line is straight with an even scale along it (or some other calibrated shape and linearity) we can deduce both the placements of the lines and the distortions of the workpiece.

It is possible to define (from the start unknown) errors for each measured point, a parameterized distortion error in the workpiece pattern, and the placement of each line. Some of the points are measured twice, or even more times, and this, together with the known shape and linearity of the measurement hardware along each of the lines, makes it possible to set up a system of equations, typically a linear system of equations, and solve for the best fit to the measured data. When the remaining error after the error resulting from the solved distortions, placements, etc ("the unmodelled error") is minimized, we have a good estimate of the distortion of the plate.

Figure 9E:
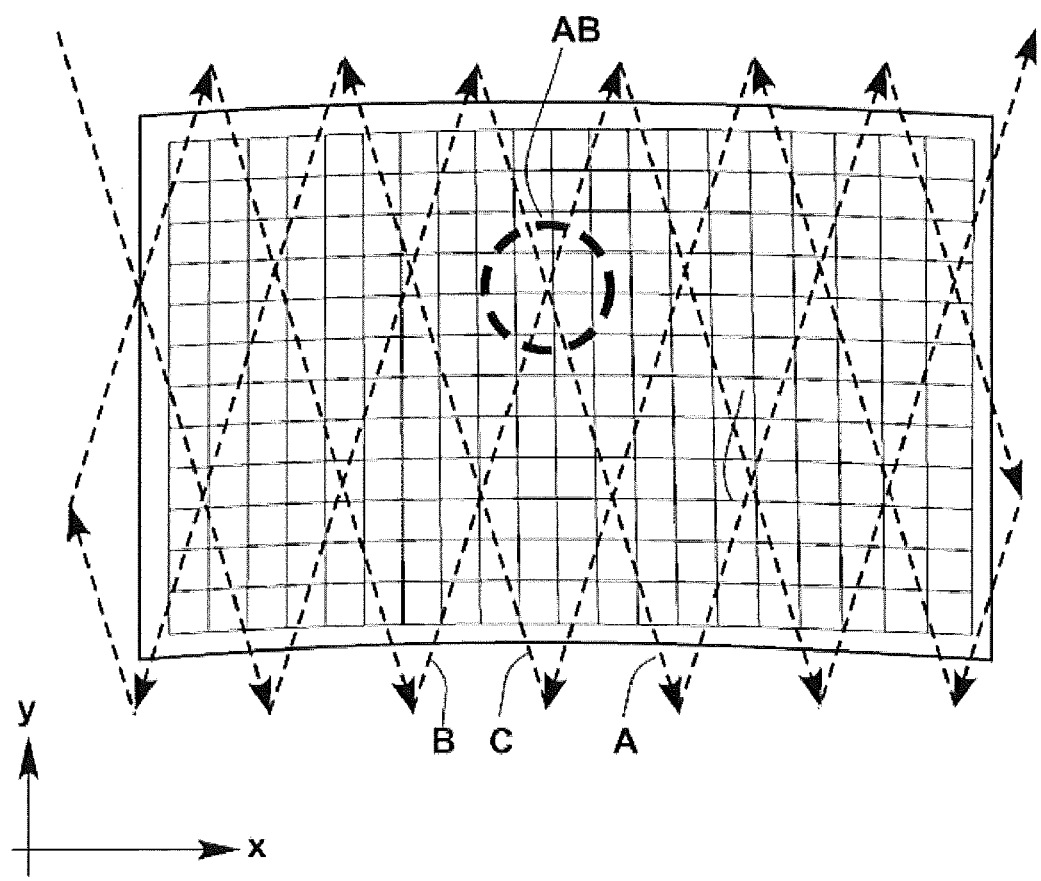
Figure 9F:
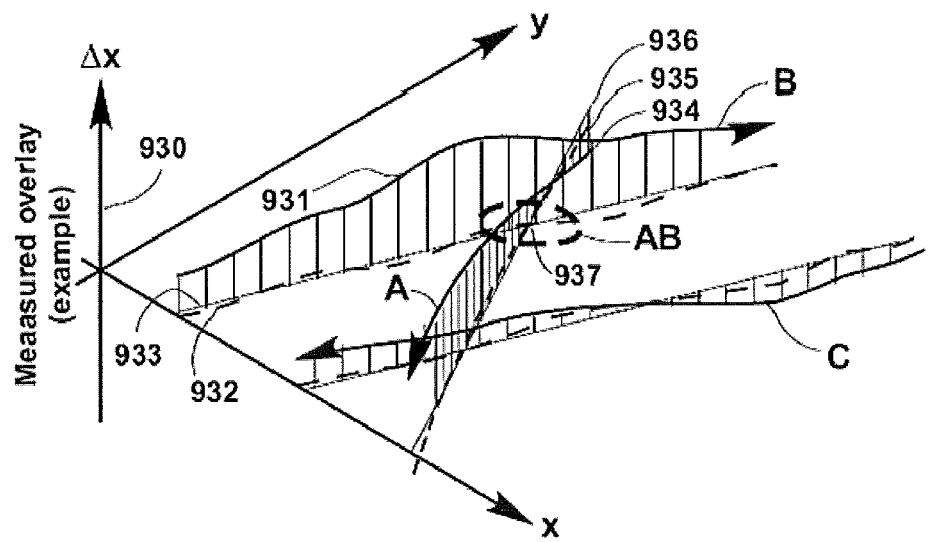

FIG. 9e shows a scanning pattern which may be used for a sensor, e.g. a position sensor not needing high position accuracy. The precision in the measured parameter is high when comparing points measured close together in time along a line A scanned by the sensor. The sensor is scanned in a criss-cross pattern over the workpiece, so that some points or areas AB are measured two or more times, e.g. by lines A and B, or A and C, crossing each other at an angle. In a general case the area AB may be scanned by more than two lines crossing at different angles. FIG. 9f shows in example form on the vertical axis 930 the data that may be measured by an overlay sensor, i.e. a camera measuring the displacement between two patterned layers in the workpiece, scanning the lines A, B, and C. The measured data 931, 934 along the lines B and A are continuous, but there are offsets between the lines due to drift in the sensor, stage or workpiece. The long-range variation along the lines may contain little real information, due to drift and other instability over longer distances, and may be removed by some form of high-pass filtering. Fourier filtering is one possibility, i.e. taking the Fourier transform, multiplying with a filter function in the frequency domain and transforming back. After filtering the measured values 932, 935 for a single point 937 should be identical for all crossing lines. One example of a mathematical way of performing both filtering and adjustment in one operation is to add Gaussian-shaped corrections centered on each crossing point, and fit the added Gaussians so that the corrected values of crossing lines coincide at each crossing. The lengths of the Gaussian functions are chosen based on the estimated deterioration of the precision with distance along the line. The magnitude of the added Gaussian corrections are chosen as to minimize the RMS variation of the corrected measurements around the zero error lines 933, 936 while satisfying the condition that crossing point 937 should have a single value. The fitting is a standard mathematical optimization problem and can be solved by known methods.

The area AB around the crossing between A and B is now spanned by two crossing filtered lines and these lines can be analyzed for mura with extremely high precision. Depending on the chosen high-pass filter cut-off and the spacing of the lines the area of high internal precision AB can be local around the crossing between two lines or it may span a network of several lines in each direction. The actual size of AB, i.e. the cut-off of the high-pass filter, can be judged from the measured data, i.e. by finding the high-pass filter that is necessary to fit the data to single points at the crossings. The generalization to three or more lines or to lines with crossing at three or more angles is straight-forward.

Operating Modes

An apparatus performing the method disclosed, in particular applied to the detection and measurement of CD- or placement-related mura, may be operated in different modes: Detection mode, High-sensitivity mode, Edge quality mode, Review mode, Camera mode, Stitching mode, Discovery mode, Intensity mode, Alignment mode, Learning mode, and Calibration mode.

FIGS. 3a, 3b, and 3c show Detection mode. 70 scans over the workpiece can be made in an hour. A workpiece of 1600× 2000 mm is more than three square meters and with an analysis time of 3 hours it will be sampled in stripes spaced 12 mm apart. The job can run faster with more separation between the stripes or the analysis can be more comprehensive with longer measure time and smaller distance between the stripes. A full-surface scan takes 12 hours. But the fact that most mura effects are either line-like or extends over some area makes the 3 hour measurement adequate in most cases. Depending on what types of mura are expected in the workpiece the sampling plan may be modified, e.g. groups of five stripes may be scanned so they form a contiguous extended camera field and they may be repeated in several positions along the workpiece.

The other parameter of the sampling plan, namely how densely the pattern is sampled in the stripe depends on the processing speed of the computer that runs the analysis. Above a certain density of measured edges the scanning must slow down or the image processing be deferred to a later time. This limit can be raised by reconfiguration with more processing power, e.g. hardware acceleration.

In high-sensitivity mode a smaller area is scanned repeatedly, e.g. the stripes A, B, and C in FIGS. 3a, 3b, and 3c. In this way instrument noise is reduced while the workpiece remains the same and signal/to noise is improved. The camera scan may be moved slightly, e.g. by 5.1 pixels in x and y, between the scans in order to average out camera artifacts.

The purpose of Edge analysis mode is to determine if the edges are smooth and uniform or if they are noisy. Edges may be noisy due to the chemical processing, the maskwriter or the materials. In Edge analysis mode a smaller area is analyzed, e.g. as described above, and statistics, e.g. spectral analysis, is performed along the edge and/or between different edges locally or between edges at different locations on the workpiece. Alternatively, a measurement window per workpiece pixel cell may be designated to edge roughness determination.

In Review mode the systems rescans a location, where a possible mura effect is suspected to occur, in High-sensitivity mode. Typically Review mode is used to verify what has been detected in Detection mode. The illumination may be changed, focus may be varied, and new data windows may be used. Review mode can be automatic or manual.

In Camera mode the entire image of a location is recorded and stored for later analysis. Multiple images the illumination and focus variations may be recorded. It is also possible to use a Barlow lens and low-sigma illumination (e.g. a laser beam) to record the pattern of scattered light and optical or numerical image enhancements may be used: e.g. multi-wavelength imaging, super-resolution processing, dark-field illumination, phase-contrast, etc.

Figure 11:
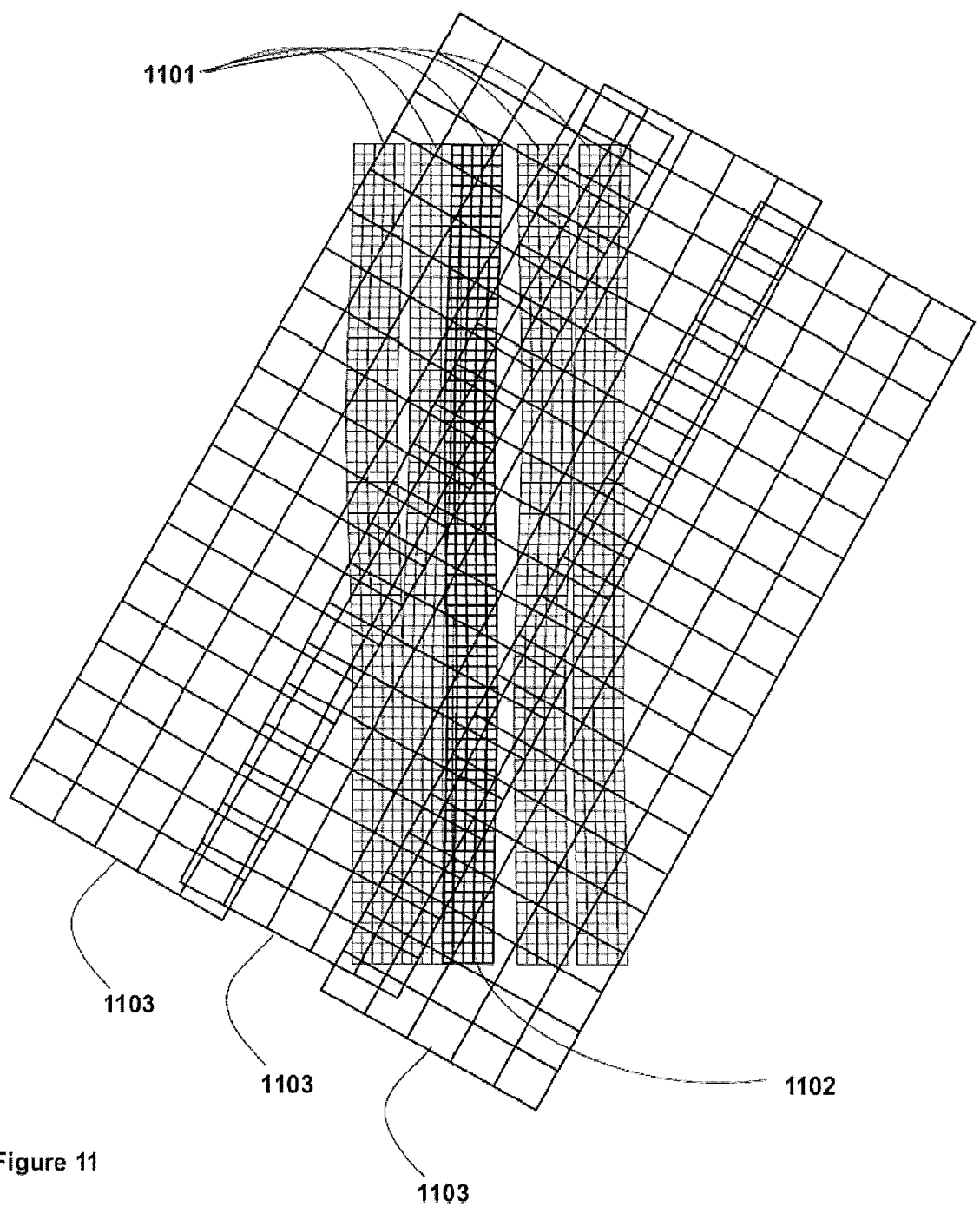
FIG. 11 gives a conceptual view of how partly overlapping extended fields (with exaggerated errors) can be stitched to measure a larger contiguous field.

Stitching mode is an operation mode where contiguous images wider than a extended field (scan stripe or measure stripe) are created. In the basic configuration the local precision in the image and within a part of the beam (e.g. within 100 mm) is extremely high. Between different stripes the position accuracy is lost due to the repositioning of the stage, deformation of the workpiece and various drifts in the system. If several stripes are recorded with a slight overlap their global position and long-range deformation can be fitted and they will form a contiguous image. Stitching of individual images itself gives an image that is not better than the scale of the single image plus the accumulated stitching error. However, as was described above the precision can be improved dramatically by clever use of a priori knowledge. A mask may be written as a sequence of stripes along one Cartesian axis, and the most important error in the mask may be a random displacement of the stripes 1101 as shown in FIG. 11. One of the stripes marked by 1102 is different from the others, which may be viewed as a mura defect. The mura detection instrument has measurement stripes 1103 where the largest uncertainty is the placement of the stripes. In the stitching mode the measurement stripes with high internal accuracy are partly overlapping and crosses several writing stripes and some figures in the pattern may be measured in two measurement stripes. This information is enough to adjust the coordinate system of the measurement stripes accurately and at the same time measure the relative displacement of the writing stripes thereby creating an image that is extended across several measurement stripes with high short-range accuracy. For long-range accuracy one can use the inherent precision of the written pattern. If the written pattern has a guaranteed (or measured) placement of 100 nm (3 sigma) the stitched image can be extended infinitely with this accuracy, while the local or semi-local (across a number of fields) may be much higher.

Figure 15A:
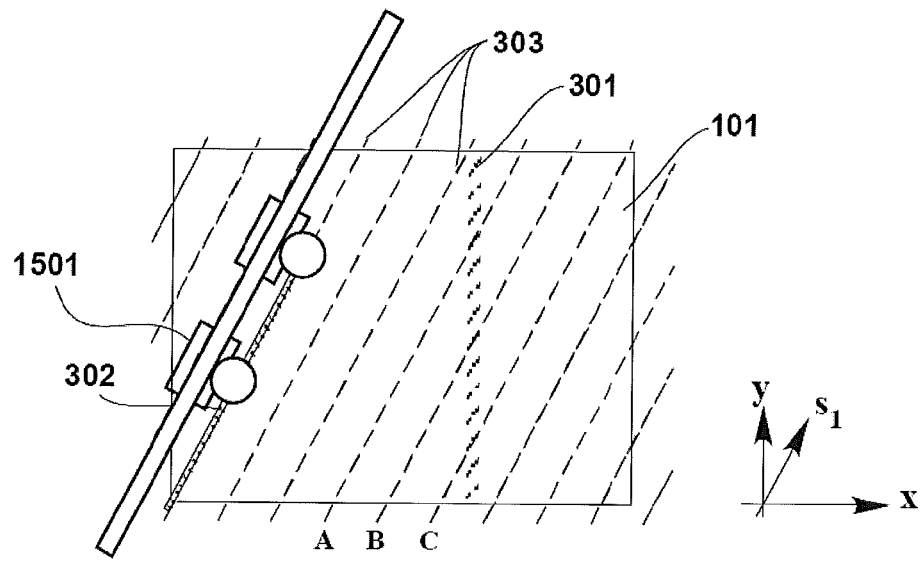
FIGS. 15a and 15b are illustrate two arrangements of cameras that could be used to supply data for direct comparison.
Figure 15B:
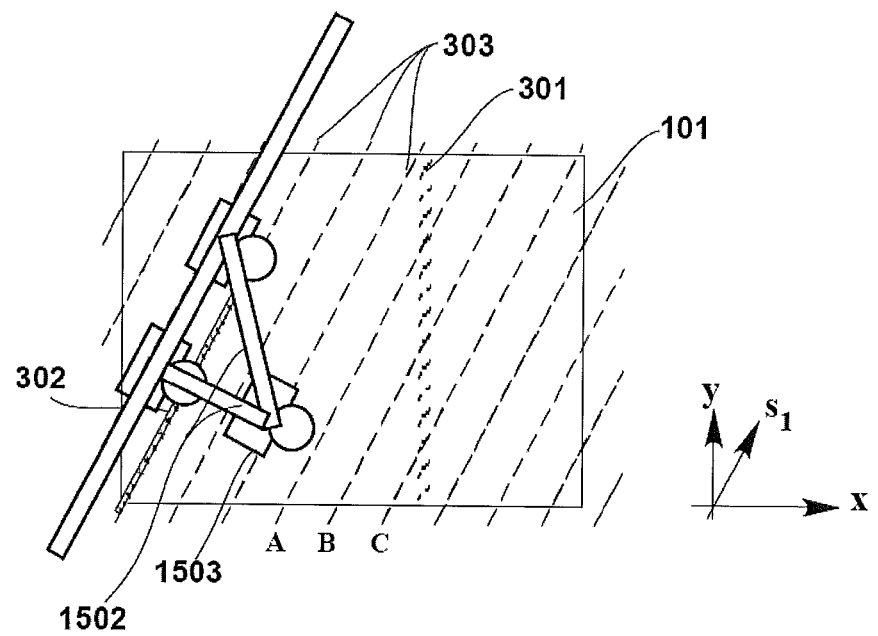

Discovery mode is for looking for other errors other than those already designated for study, e.g. errors which cannot be described as displacements of the edges chosen in the job description. An example could be a mura variation of the chevrons in FIG. 4d. Discovery mode searches for any nonrepeating variations in a repeated pattern by image processing of the captured bitmap, e.g. by comparing a cell to a neighboring cell, to a static comparison cell, to an accumulated average cell, or to simulated data. The image variations may be in placement or in intensity. Alternatively, two or more cameras can be used in a fixed geometrical relationship and data from the two cameras compared in real time. FIGS. 15*a* and 15*b* are variations on FIGS. 3*a*, 3*b*, and 3*c* which illustrate two arrangements of cameras that could be used to supply data for direct comparison. In FIG. 15*a*, we add a second camera 1501 positioned along the same arm that caries the first camera. A rigid coupling, e.g., using a Zerodur® bar between the cameras, would afford extremely low thermal expansion. Precise spacing between the cameras could be adjusted along the bar or could be adjusted by using a relatively small memory buffer to adjust the offset between the cameras. Extremely accurate lateral stability in positioning of the first and second cameras may be useful for detecting placement errors along stitching boundaries. FIG. 15*b* shows a two dimensional configuration of cameras, adding one or more additional cameras 1502, 1503 to supplement the first camera.

Various statistical methods can be used for extracting data, e.g. finding points in the image that has the highest variability from cell to cell and track them. No assumptions except the repetition pitches are needed, or alternatively critical areas may be pre-assigned. Discovery mode is slower than Detection mode and may be run as a preparation for detection mode or sampling less area in every workpiece or a sample of the workpieces. Typically Camera mode and Discovery mode are used for engineering studies or for debugging of the production system.

Intensity mode is an adaption for patterns that are not well resolved by the optics. Detection mode normally assumes that the edge is straight and fully formed, so that the position can be accurately estimated from the image of the edge. For very thin lines and involuted 2D features such analysis may be difficult. In these cases the gray tone in the image of an only partially resolved feature may be used as a measure of the features shape and/or size. Intensity mode may be used concurrently with Detection mode. Similar windows used for edge detection in FIGS. 3*a*, 3*b*, and 3*c* are designated for intensity measurement.

In Alignment mode the system is searching for one or several fiducials or prominent pattern features in order to align the internal coordinate system to the workpiece. This is common in machine vision applications and may be using commercial software as provided by Dalsa, Hamamatsu or other companies.

In Learning mode the camera records an image including edges to be measured and tests the precision and robustness of the edge measurement algorithm. The illumination and focus is varied and the parameters of the edge model are adjusted to improve detection robustness. Learning mode may be automatic or manual and automatic learning may be run at the start of every job.

There are two calibrations that need to be done: the straightness of the beam and the linearity across the extended field. For both of them it is possible to accumulate a calibration by integration of all measured errors over time. In the long run true errors should average out to zero and any non-zero average can be attributed to the metrology system. However, this is a slow method and it is sensitive to the assumption that the measured errors are random. A faster and more direct method may be needed. The straightness can be calibrated by rotation of a workpiece by 180 degrees and measurement of the same features in the two orientations. Further errors can be found if the workpiece is translated, so that the same features are measured at different position along the beam. The bending of the beam which best models the actual measurements is the calibrated shape. In principle three measurements 0, 180 and 180 degrees translated along the beam should suffice to determine the shape of the beam. More measurements will give more redundancy and better accuracy.

The calibration of the linearity across the field may be done similarly: measuring the distance between two features when the vector between them is along and across the field, since the accuracy over short distances along the field is a few nanometers. For calibration of the field it is also possible to measure a pattern which has been qualified by a small-area metrology system such as IPRO from Vistec, Germany. The qualified pattern can be kept with, or preferably mounted in, the system as a calibration reference during the lifetime of the system.

Figure 10:
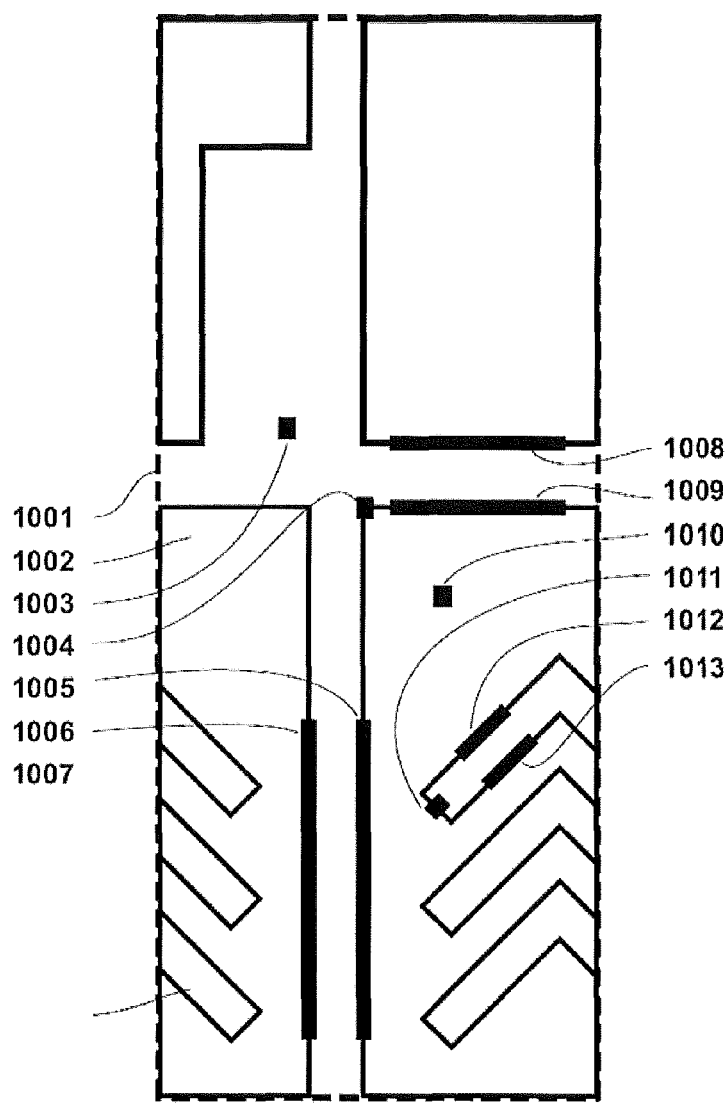
FIG. 10 illustrates how different areas and points in the image can be used simultaneously for different detection modes.

FIG. 10 shows how different modes can be used simultaneously during the same job. The picture shows one cell 1001, same as in FIG. 4*b*, with a repeating part of a TFT pattern 1002. Four Manhattan edges 1005, 1006, 1008, 1009 are designated for horizontal and vertical CD and placement measurements. Two more 1012, 1013 for small feature 45 degree CD. Two windows are designated for Intensity mode, one on a corner 1004 and one on the end of the chevron 1011 which may be predicted to be sensitive. Two of the edges 1006, 1009 are also designated for edge analysis. Finally two windows 1003, 1010 far from any edges are designated as reference for the camera clear and dark levels.

The technology disclosed by means of examples and many specifics can be implemented in alternative ways. The extended field may be created by line-scan cameras or as a sequence of area images and many features of the technology disclosed would remain unchanged. The mathematical analysis can be done in many ways and many of the principles laid down here would still hold. The movements of camera and glass could be implemented in other ways and still preserve the relative movements.

Apparatus for Detection of Mura by Light Scattering

Light scattering is extremely sensitive as a detection method for small distance variations as well as variations in film thickness, overlay and edge shape. If may also detect edge roughness. Variations of the light scattered in a specific angle which depends on the pattern may be quantified and used as a measure of local pattern variations as described in the prior art patent JP25233869A2. A different method is to use a fixed angle of illumination, e.g. perpendicular to the surface, and image the angles of light scattering onto points on an image sensor. Such a sensor will simultaneously quantify many thousand frequency components of the pattern, making it more versatile than the prior art method. Such an angle-resolved scatterometer may be combined with the sampling and data reduction methods described above to find areas, blemishes, or bands with different properties. The scatterometry data can be used for explorations of variations in the pattern. The detected pattern can be empirically correlated to quality problems after assembly, or in other cases detected changes may give no visible effect. Known variations may be modelled by optical diffraction software, e.g. Panoramic EM-suite by PanoramicTech, USA. It is likely that the utility of scatterometry as a diagnostic for mura will grow with experience and maturity of the method. It is useful to combine the scatterometry sensor with software for analyzing the data, comparing to electrical, optical and visual tests and develop classification of the detected variations together with tolerance limits for types of variations which prove to be significant. The learning software may make use of artificial intelligence, data mining and/or neural networks as well as interactive human development of classification rules.

Figure 13A:
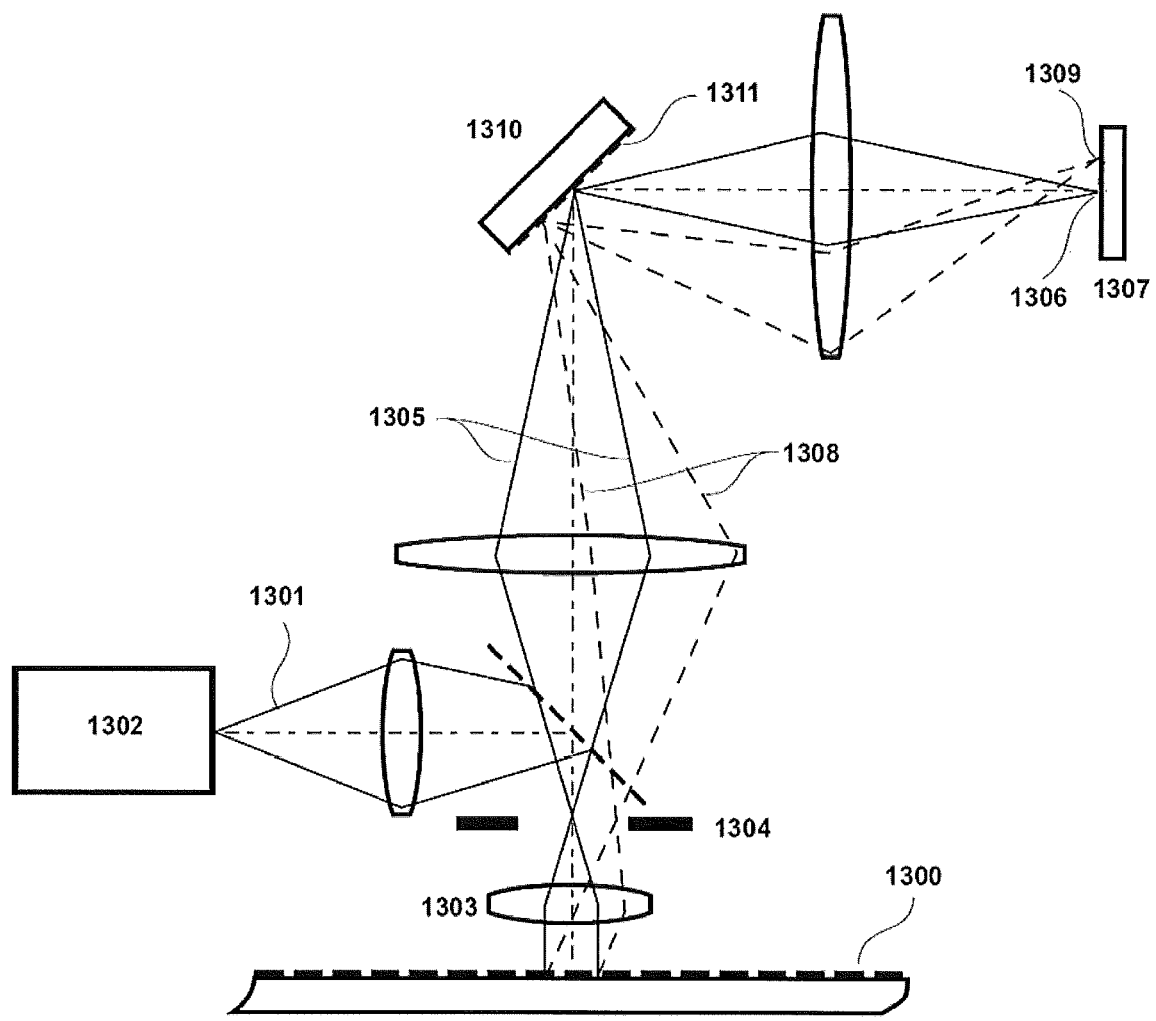
FIGS. 13a-d show example embodiments of a sensor for pattern variations based on light scattering.

FIGS. 13a-d shows example embodiments of sensors for angle-resolved scatterometry to be used scanned over the workpiece for mura detection. FIG. 13a shows a workpiece with a pattern 1300 illuminated by light 1301, e.g. laser light, from a light source 1302 through a lens 1303 having an aperture 1304. The specularly reflected light 1305 is passed through an optical system and forms a point 1306 on an image sensor 1307, e.g. a CCD sensor. Light that is scattered by the pattern 1300 goes a different path 1308 and ends up in another position 1309 on the image sensor 1307. Each position on the image sensor 1307 corresponds to one two-dimensional spatial frequency component in the pattern 1300. A regular pattern, e.g. an LCD pattern, gives a number of illuminated points 1309 on the image sensor 1307. Minute changes in the pattern lead to changes in the relative strength of the points 1307 and the spot pattern formed on the image sensor 1307 can be used to quantify variations in the pattern. For some patterns the 0:th order (the specular beam) is much stronger than any of the other spots and the dynamic range of the camera will not be enough to capture both. One remedy is to spread the spots into small patches, e.g. by defocusing or using a weak diffuser. Another remedy is to overexpose the 0:th order, and possibly other strong orders as well, in order to get a good exposure for the information-carrying weaker spots. Still another is to use a sensor with very high dynamic range, e.g. a CMOS sensor with logarithmic response, or two use two sensors with different range, e.g. split the beam into one strong and one weak beam and direct them to different sensor. FIG. 13a shows a preferred embodiment with a fixed or computer-controlled spatial filter 1310 to filter out the strong spots. The filter in the FIG. 1310 is shown as reflective, but transmissive filters are equally useful. The spot image is formed on the spatial filter, which may be a spatial light modulator, e.g. with micromirrors 1311 as in a Texas Instruments DMD chip, or with an LCD cell. Other filters attenuating light that is scattered on selected directions off the workpiece may be used. The filter is set up to create a filter function which attenuates or masks the strong spots, thereby making weak details in the scattered light easier to resolve.

Figure 13B:
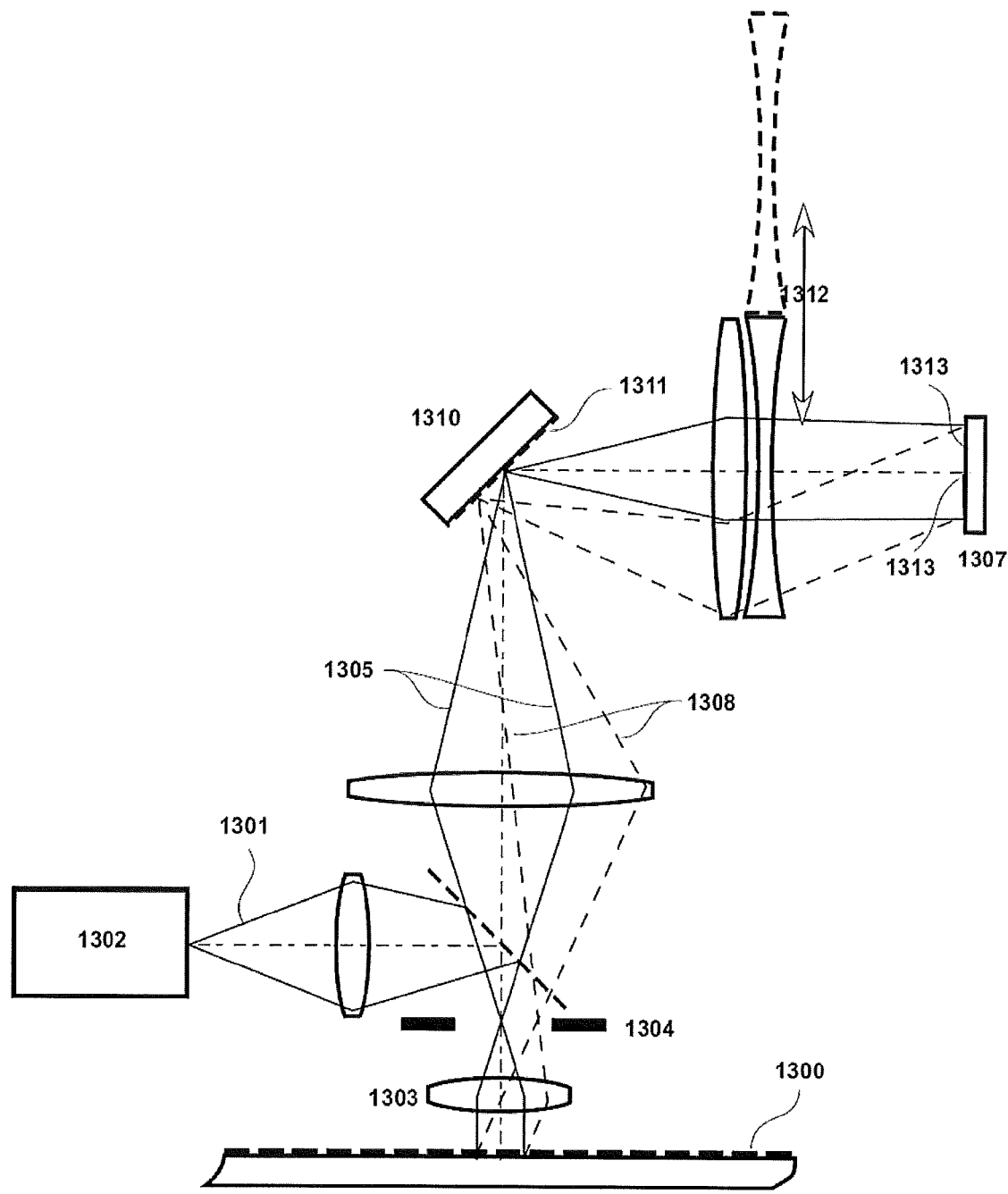

In FIG. 13b the after-the-workpiece optics has been reconfigured by a flip-in lens 1302 so that the scattered light, filtered by the angle filter 1310, is made to form an image 1313 of the workpiece on the sensor 1307. This image will highlight edges and small features and changes in these will be exaggerated. Analyzing this image 1313, i.e. measuring intensities at designated points or comparing images from different areas which are expected to be identical, may give a more sensitive detection of the errors which give rise to mura. Multiple images of the same area may be taken in a sequence with varying filtering, increasing the detection sensitivity and strengthening the diagnostic power of the method.

Typically the area mode of FIG. 13a, where the average scattering into different angles, and the image mode of FIG. 13b, where the scattering of features on the workpiece into selected angles are monitored or measured, may serve different purposes and they can be used in different situations. The area mode may be used for overview of a workpiece and any found suspect areas may be analyzed in the image mode, possibly using a sequence of images with different settings of the angle filter 1310.

Figure 13C:
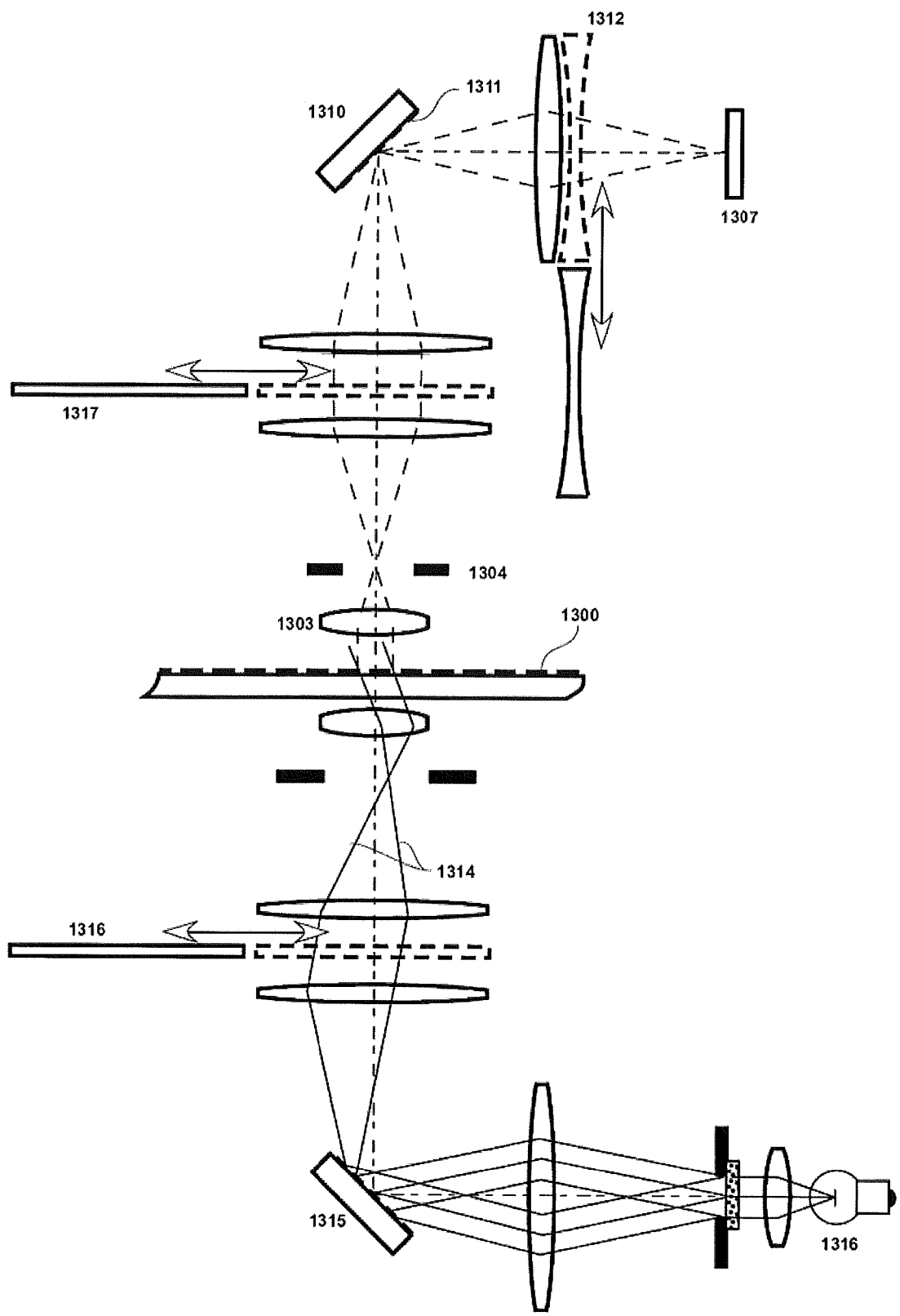

FIG. 13c shows an example embodiment of the sensor with three main points: First, the sensor may use transmitted light 1314. Second, the illuminator may have a spatial filter 1315 or beam deflector to vary the angle or angles of incidence at the workpiece. Thirdly, filters (e.g. color filters or polarization filters) may be introduced in the beam path in both the illumination and image side of the sensor to change or enhance the detection. The light source is shown as an incandescent source 1316, i.e. a tungsten filament with a diffuser 1317, but other light sources may be used, e.g. lasers, LEDs, gas discharge lamp, etc.

Figure 13D:
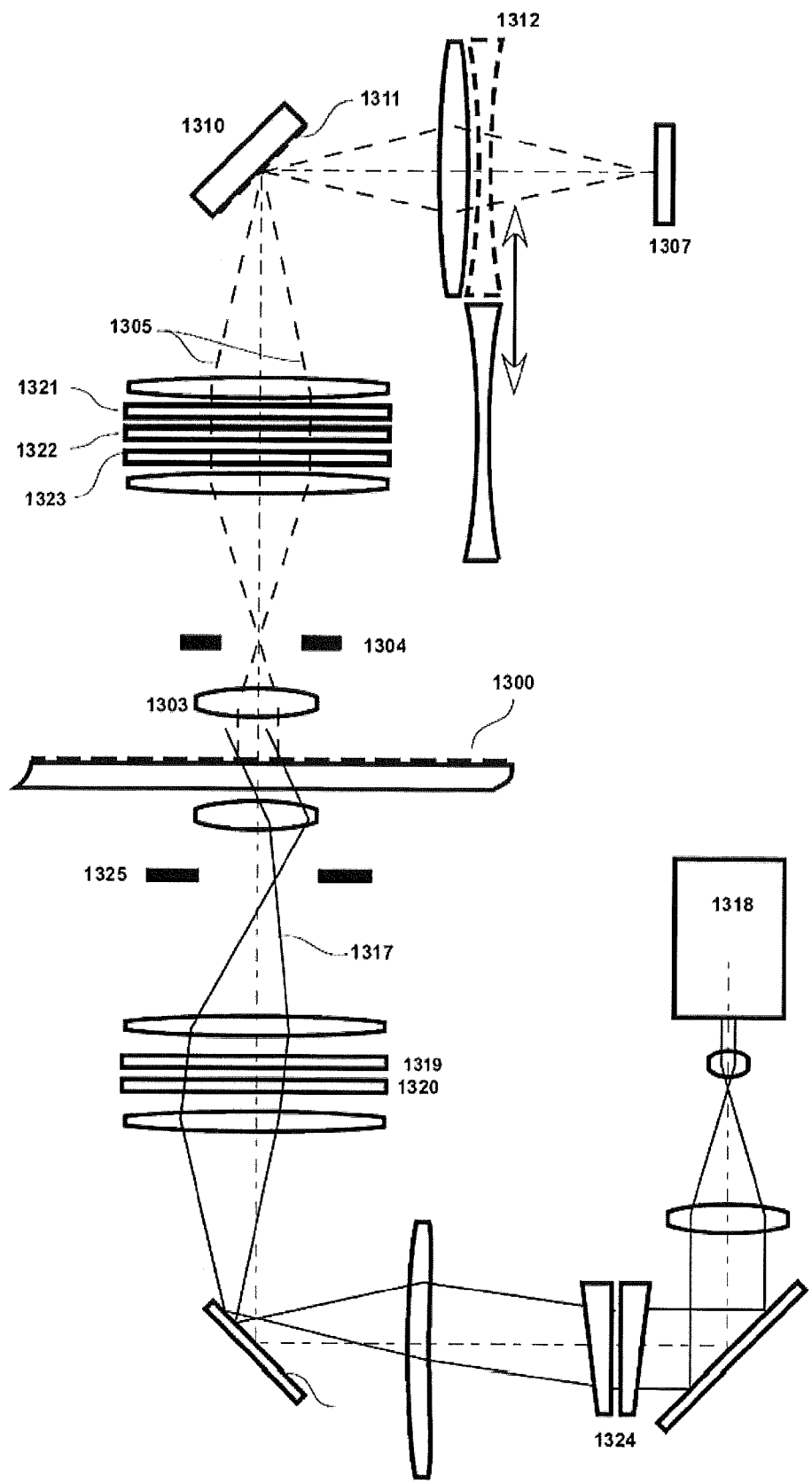

FIG. 13d illustrates an example embodiment of a mura sensor using transmitted light 1317 from a laser source 1318. The laser may be polarized and the polarization state impinging on the workpiece pattern 1300 can be given any desired polarization state by adjustable polarization components 1319, 1320, e.g. a quarter-wave plate and a half-wave plate. The imaging side may contain a polarizing filter 1321 and components 1322, 1323, e.g. a quarter-wave plate and a half-wave plate, for changing the polarization state from the workpiece which reaches the detector 1307. The detector can be configured to capture diffraction angles or images of the workpiece, e.g. with a flip-in lens 1312. The light 1317 impinging on the pattern 1300 can be scanned in angle by a beam deflector, e.g. by actuated mirrors, prisms or lenses or and in the shown example by rotating wedges.

The errors, i.e. the homogeneities, in the pattern can be qualitatively detected or quantitatively measured by the sensor. For the highest resolution to changes in the pattern the several images are recorded with different settings of angles and/or polarizations and the images are then compared to a simulated model. The exact modelling can be used to create a linear approximation model, which may by used to quantify small changes in the characteristics of a feature in a pattern around the typical value of the characteristic. Software suitable for modelling is Panoramic EM-Suite made by PanoramicTech, USA. Other suitable software is made by Timbre, USA.

The example embodiment shown in FIG. 13d, with arbitrarily controlled input and output polarizations, allows the measurement of the Mueller matrix coefficients, angle-resolved and averaged over a small area, or alternatively the Mueller matrix coefficients average over some angle range from each point of the pattern. The example apparatus combines the ability to rapidly search a large workpiece for anomalies, and the analyzing conditions, e.g. input and output polarizations and angle ranges such as clear-field and dark-field imaging, can be chosen to maximize the sensitivity to errors that are known to be relevant and suppress the response to known irrelevant ones.

Once a suspect area has been found, and a closer analysis is needed, a review mode can be entered where the pattern is analyzed using a sequence of images formed by selected polarization and angle ranges. Both the rapid scanning of large areas and the detailed analysis of small areas are non-destructive and are suitable for quality control and process debugging in a production environment.

Classically the term scatterometry is more related to FIG. 13a, i.e. scattering from an area, than to FIG. 13b, i.e. imaging by light selected by scattering angle and polarization. Some of the methods used in microscopy for contrast enhancement, e.g. phase contrast, interference, Nomarski-differential interference contrast, etc. (see Hanry Yu, et al., "Multi-Modality Microscopy") may be adapted to the technology disclosed to enhance the contrast of difficult objects.

Multi-spectral imaging, which separates image information by spectral band, can be used to provide interesting information. By means for spectral separation of image information, we mean analyzing many narrow bands of image information. In one structure, narrow bands can successively be used to image part of a surface. Alternatively, the narrow bands can be used simultaneously. Processing of the narrow bands can be separated in time, in direction of illumination or by filtering or splitting image information prior to capture. In time, different frequencies of light can be projected successively onto the workpiece and the response detected by the sensor. Or, a broad spectrum light can be projected and a variety of filters applied successively for detection using a single sensor. A broad spectrum light also could be used with a plurality of sensor that simultaneously evaluate different spectral base. For instance, the image information could be divided into several parts and filters applied to sample narrow bands of image information with different sensors. (This is similar to what a camera typically does, with RGB filters, but the filters can be selected for analytical purposes, instead of image capture.) Alternatively, the image information could be diffracted using a prism or grating and sensors aligned in different positions corresponding to different wave bands. Yet another alternative is to use multiple narrow bands projected along different axes and evaluated by different sensors. Analyzing the difference in results produced in different wave bands provides interesting information and opportunities for comparison of results in one band versus another.

A scattering sensor may be used for patterns with features down to a fraction of a wavelength, making it useful for mura detection not only on display panels and masks, but also on semiconductor masks and wafers with image sensors, memory devices and other patterns with high repetition and tight uniformity requirements.

The scatterometry sensor may be combined with an imaging camera for pattern image metrology or it may be separate. If separate, the sensor and camera may be scanned together over the workpiece and collecting data simultaneously i.e. during the same mechanical motion. In general the same mura detection system may have several sensors scanning the workpiece simultaneously or sequentially.

Other Sensors

Many other sensors may be used with the technology disclosed. Scanning the sensor across the dominating directions of mura gives high precision, efficient data reduction, and suppression of workpiece distortion and drift and other artifacts of the sensor or sensor positioning systems. Examples of other sensors which may be used with described methods are electron and ion beam sensors for accurate determination of CD, placement or shape of small features, e.g. in semiconductor image sensors and memory devices. Particle beams may be used in a vacuum tank, with a small differentially pumped open chamber, or with a short path in the ambient.

One physical mechanism which may contribute to mura is a variation in the thickness, composition, stress or structure of a thin film, e.g. an ITO, oxide, semiconductor, polymer or metal film. Sensors for these changes may be used with the technology disclosed: e.g. spectroscopic, reflectometric, polarimetric, ellipsometric, magnetic, near-field or stylus scanning, particle backscattering, or optical or x-ray fluorescence sensors, as well as sensors based on acoustic waves in the material.

Another mechanism which may contribute to mura is surface condition which may influence the fields and thereby the alignment of the liquid crystals, e.g. charges embedded in polymer films. The invention may use a capacitive probe to sample charge anomalies when scanning across the surface of a workpiece, or a Kelvin probe to probe the surface potential and its changes. Capacitive probes and Kelvin probes may also be used to sample the capacitance of the nodes in display panels and the impedance and leakage of transistors in transistor arrays.

Height and flatness variations may be sampled by an interferometric sensor having one beam probing the workpiece and a reference beam going a reference path, such as a Michelson, Mach-Zehnder, Mireau or Linnik or similar interferometer (P. Hariharan, *Optical Interferometry*, 2nd edition, Academic Press, San Diego, USA, 2003) or the amplitude measuring instruments described in US (*Micronic-Sandstrom filed spring* 2007 *amplitude imaging*) which is hereby included by reference or interferometric systems described in U.S. Pat. No. 7,002,691 and other patents related to so called Direct-to-Digital Holography.

SOME PARTICULAR EMBODIMENTS

Technology disclosed can be practiced as a method or device. One method embodiment is for detection and quantification of mura defects in a pattern on a workpiece. The method uses a sensor for a parameter to be analyzed. It may include providing the sensor. It includes extending a field of the sensor to an extended sensor field by mechanically moving the sensor. The extended sensor field created by movement crosses at least one dominating direction of mura defects at an angle, such as 20 to 90 degrees. Crossing the dominating direction of the defects at an angle provides a sequence of measurements with high internal precision among them. The sequence of measurements crosses the mura defects and extends into a reference area.

One aspect of the method is that the measurements of mura defects and the reference area are separated temporally by less than 10 seconds or even by less than one second. Preferably, the movement that creates the extended sensor field is a one dimensional movement.

Another aspect of the method is that the movement proceeds linearly in a direction that is not parallel to Cartesian axes of features patterned on the workpiece. Typical features on a workpiece form a so-called Manhattan geometry. The axes of Manhattan geometry are along the street and the vertical edges of buildings. Many workpieces have features laid out as variations on this geometry.

In some embodiments, the parameter to be analyzed is geometrical placement of an edge of a repeated figure. According to this embodiment, the movement that creates the extended sensor field has a precision better than 30 nanometers across a distance of 30 millimeters. In another embodiment, the precision is better than 10 nanometers across a distance of 100 millimeters.

The sensor or detector used for analysis may be a high-resolution camera, such as a TDI camera.

Sometimes, a sampling plan is used to define a plurality of metrology windows within the extended sensor field and placement of the edge of a feature is determined from pixel data within the metrology windows.

Another aspect of this method may be applying the extended sensor field to form an oblique stripe across at least part of the workpiece. The workpiece is sampled by a sparse sequence of such stripes.

Analysis of collected data can provide a variety of results. Mura defects may be separated from noise and drift by their different geometrical behavior in the measured data. Mura defects may be classified in categories based on their different spatial signatures. A test result may be presented as describing a mura type, location and severity.

An alternative embodiment is an apparatus for detecting and quantifying mura defects on a workpiece. This device may include support for the workpiece, a linear scanning stage that carries a high-resolution camera across the surface the workpiece in a direction nonparallel to a least one dominating direction of mura. It further includes a computer acquiring image data from the camera with software adapted to quantify the placement of edges in the image data and to correlate the placement with dominating directions of mura.

The apparatus further may include a second camera positioned in a fixed position relative to the first camera. The computer acquires data from both cameras. The software compares the data from the two cameras, using a data buffer, if necessary, to adjust the relative position of the image data from at least one the two cameras.

Another aspect of the apparatus, applicable to embodiments using one or more cameras, is for the software to be adapted to report placement errors detected along stitching boundaries in the repeating pattern.

Other devices practicing the methods described above are described in the preceding text.

We claim as follows:

1. A method for detection and quantification of mura defects in a pattern on a workpiece including:
   providing a sensor for a parameter to be analyzed,
   extending a field of the sensor to an extended sensor field by a mechanical movement of the sensor,
   wherein the extended sensor field crosses at least one dominating direction of mura defects at an angle, thereby providing a sequence of measurements with high internal precision between them, said sequence of measurements crossing the mura defects and extending into a reference area, wherein the mura defects are separated from noise and drift by their different geometrical behavior in the sequence of measurements.

2. The method of claim 1, wherein the measurements of the mura defects and the reference area are separated temporally by less than 10 seconds.

3. The method of claim 2, wherein said parameter is geometrical placement of an edge of a repeated feature and the movement has a precision better than 30 nm across a distance of 30 mm.

4. The method of claim 3, wherein the extended sensor field forms an oblique stripe across at least part of the workpiece and the workpiece is sampled by a sparse sequence of such stripes.

5. The method of claim 3, wherein the mura detects are classified in categories based on their different spatial signatures.

6. The method of claim 3, wherein the test result is presented as mura type, location, and severity.

7. The method of claim 2, wherein said parameter is geometrical placement of an edge of a repeated feature and the movement has a precision better than 10 nm across a distance of 100 mm.

8. The method of claim 7, wherein a sampling plan defines metrology windows within the extended sensor field and placement of the edge of a feature is determined from pixel data within said metrology windows.

9. The method of claim 1, wherein the measurements of the mura defects and the reference area are separated temporally by less than 1 second.

10. The method of claim 1, wherein the movement is a linear movement in a direction not parallel to Cartesian axes of features exposed on the workpiece.

11. An apparatus for detecting and quantifying mura defects on a workpiece including:
    a support for the workpiece,
    a linear scanning stage carrying a first high-resolution camera across a surface of the workpiece in a direction non-parallel to one or more expected dominating directions of mura, and
    a computer acquiring image data from the first camera with software adapted to quantify the placement of edges in the image data and to correlate said placement with the expected dominating directions of mura and adapted to separate the mura defects from noise and drift by their different geometrical behavior in the image data.

12. The apparatus of claim 11, further including:
    a second high-resolution camera carried along in a fixed position relative to the first camera;
    the computer acquiring image data from the second camera; and
    the software adapted to compare the image data from the first and second cameras for at least one repeating pattern imaged from the workpiece.

13. The apparatus of claim 11, further including the software adapted to report placement errors detected along stitching boundaries in the repeating pattern.

14. The apparatus of claim 11, further including means for spectral separation of image information into spectral bands in or before the camera and the software adapted to compare the image information in a plurality of the spectral bands.

* * * * *